US 10,895,534 B2

(12) United States Patent
Finkelstein et al.

(10) Patent No.: US 10,895,534 B2
(45) Date of Patent: Jan. 19, 2021

(54) METHOD AND SYSTEM FOR FLUORESCENCE LIFETIME BASED SEQUENCING

(71) Applicant: ILLUMINA, INC., San Diego, CA (US)

(72) Inventors: Hod Finkelstein, El Cerrito, CA (US); Cheng Frank Zhong, Fremont, CA (US); Eliane H. Trepagnier, San Francisco, CA (US)

(73) Assignee: Illumina, Inc., San Diego, CA (US)

( * ) Notice: Subject to any disclaimer, the term of this patent is extended or adjusted under 35 U.S.C. 154(b) by 460 days.

(21) Appl. No.: 14/619,287

(22) PCT Filed: Mar. 8, 2013

(86) PCT No.: PCT/US2013/029837
§ 371 (c)(1),
(2) Date: Feb. 11, 2015

(87) PCT Pub. No.: WO2014/031157
PCT Pub. Date: Feb. 27, 2014

(65) Prior Publication Data
US 2015/0293021 A1    Oct. 15, 2015

Related U.S. Application Data

(60) Provisional application No. 61/684,984, filed on Aug. 20, 2012.

(51) Int. Cl.
*H01L 31/107*        (2006.01)
*H01L 31/055*        (2014.01)
(Continued)

(52) U.S. Cl.
CPC .... *G01N 21/6408* (2013.01); *B01L 3/502715* (2013.01); *C12Q 1/6869* (2013.01);
(Continued)

(58) Field of Classification Search
None
See application file for complete search history.

(56) References Cited

U.S. PATENT DOCUMENTS 5,641,658 A    6/1997  Adams et al.
5,986,297 A    11/1999 Guidash et al.
(Continued)

FOREIGN PATENT DOCUMENTS

IE    20060447    4/2009
WO    9106678     5/1991
(Continued)

OTHER PUBLICATIONS

International Search Report and Written Opinion; PCT/US2013/029837; dated Aug. 3, 2013; 7 pages.
(Continued)

*Primary Examiner* — Neil N Turk
(74) *Attorney, Agent, or Firm* — Illumina, Inc.

(57) ABSTRACT

An integrated detection, flow cell and photonics (DFP) device is provided that comprises a substrate having an array of pixel elements that sense photons during active periods. The substrate and pixel elements form an IC photon detection layer. At least one wave guide is formed on the IC photo detection layer as a photonics layer. An optical isolation layer is formed over at least a portion of the wave guide. A collection of photo resist (PR) walls patterned to define at least one flow cell channel that is configured to direct fluid along a fluid flow path. The wave guides align to extend along the fluid flow path. The flow cell channel is configured to receive samples at sample sites that align with the array of pixel elements.

20 Claims, 17 Drawing Sheets

(51) Int. Cl.

| | |
|---|---|
| *G01S 7/4863* | (2020.01) |
| *G01S 7/4865* | (2020.01) |
| *B01L 3/00* | (2006.01) |
| *G01N 21/64* | (2006.01) |
| *G01N 21/77* | (2006.01) |
| *G01N 21/05* | (2006.01) |
| *C12Q 1/6869* | (2018.01) |

(52) U.S. Cl.
CPC .......... *G01N 21/05* (2013.01); *G01N 21/648* (2013.01); *G01N 21/6428* (2013.01); *G01N 21/6452* (2013.01); *G01N 21/6454* (2013.01); *G01N 21/7703* (2013.01); *G01S 7/4863* (2013.01); *G01S 7/4865* (2013.01); *H01L 31/055* (2013.01); *H01L 31/107* (2013.01); *G01N 2201/06113* (2013.01); *G01N 2201/10* (2013.01)

(56) References Cited

U.S. PATENT DOCUMENTS

| | | |
|---|---|---|
| 6,192,168 B1 | 2/2001 | Feldstein et al. |
| 6,210,891 B1 | 4/2001 | Nyren et al. |
| 6,258,568 B1 | 7/2001 | Nyren et al. |
| 6,274,320 B1 | 8/2001 | Rothberg et al. |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,315,019 B2 | 1/2008 | Turner |
| 7,329,492 B2 | 2/2008 | Hardin et al. |
| 7,329,860 B2 | 2/2008 | Feng et al. |
| 7,405,281 B2 | 7/2008 | Xu et al. |
| 8,039,817 B2 | 10/2011 | Feng et al. |
| 8,241,573 B2 | 8/2012 | Banerjee et al. |
| 2002/0055100 A1 | 5/2002 | Kawashima et al. |
| 2004/0002090 A1 | 1/2004 | Mayer et al. |
| 2004/0091862 A1 | 5/2004 | Brandenburg et al. |
| 2004/0096853 A1 | 5/2004 | Mayer et al. |
| 2005/0153320 A1 | 7/2005 | Jerron et al. |
| 2006/0051244 A1 | 3/2006 | Lehmann et al. |
| 2006/0202129 A1* | 9/2006 | Niclass .................. G01T 1/248 250/370.14 |
| 2007/0085025 A1 | 4/2007 | Eggeling et al. |
| 2007/0099208 A1 | 5/2007 | Drmanac et al. |
| 2007/0128624 A1 | 6/2007 | Gormley et al. |
| 2007/0250274 A1 | 10/2007 | Volkov et al. |
| 2008/0009420 A1 | 1/2008 | Schroth et al. |
| 2008/0091005 A1 | 4/2008 | Wang et al. |
| 2008/0108082 A1 | 5/2008 | Rank et al. |
| 2008/0225140 A1 | 9/2008 | Raynor et al. |
| 2009/0014658 A1 | 1/2009 | Cottier et al. |
| 2009/0247414 A1 | 10/2009 | Obradovic et al. |
| 2010/0053390 A1 | 3/2010 | Takubo et al. |
| 2010/0085340 A1 | 4/2010 | Omoto et al. |
| 2010/0157086 A1 | 6/2010 | Segale |
| 2011/0096157 A1 | 4/2011 | Fine et al. |
| 2012/0021525 A1 | 1/2012 | Fehr et al. |
| 2012/0156714 A1 | 6/2012 | O'Brien et al. |
| 2012/0200749 A1 | 8/2012 | Boettiger et al. |

FOREIGN PATENT DOCUMENTS

| | | |
|---|---|---|
| WO | 04018497 | 3/2004 |
| WO | 07123744 | 11/2007 |
| WO | 2009056831 | 5/2009 |
| WO | 2010068884 | 6/2010 |

OTHER PUBLICATIONS

Toshihiko Baba et al., "Light Localizations in Photonic Crystal Light Defect Waveguides", IEE Journal of Selected Topics in Quantum Electroncis, vol. 10, No. 3, May/Jun. 2004.

David R. Bently et al, "Accurate whole human genome sequencing using reversible terminator chemistry", doi: 10.1038/nature07517, vol. 456, Nov. 6, 2008, pp. 53-59, including supplemental information pp. 1-55.

International Preliminary Report on Patentability; PCT/US2013/029837; filed Mar. 8, 2013; dated Mar. 5, 2015; 15 pages.

Joo, Chirlmin, et al., "Advances in Single-Molecule Fluorescence Methods for Molecular Biology", Annu. Rev. Biochem. 2008, 77:51-76.

Konig, Karsten, et al., "Multiphoton Flim and Spectral Imaging of Cells and Tissues", Proc. of SPIE vol. 5323, 2004, pp. 240-251.

Lu, H. Peter, "Single-Molecule Study of Protein-Protein and Protein-DNA Interaction Dynamics", Methods in Molecular Biology, ISSN 1064-3745; vol. 1045, Humana Press, US vol. 305, 2005, pp. 385-413.

Kennedy, G. , et al., "Fluorescence Lifetime Imaging Endoscopy", Endoscopic Microscopy VI, vol. 7893, No. 1, Feb. 10, 2011, pp. 1-6.

Altenbach, Kristen et al., "In vivo FLIM-FRET measurements of recombinant proteins expressed in filamentous fungi", Fungal Biology Reviews 23 (2009) 67-71.

Fiserova, Eva et al., "Mean fluorescence lifetime and its error", Journal of Luminescence 132 (2012) 2059-2064.

Stoppa, David et al., "Single-Photon Avalanche Diode CMOS Sensor for Time-Resolved Fluorescence Measurements", IEEE Sensors Journal, vol. 9, No. 9, Sep. 1, 2009, 1084-1090.

Gersbach, M. et al, "High-Frame-rate TCSPC-FILM Using a Novel SPAD-based Image Sensor", Proceedings of SPIE, vol. 7780, Aug. 19, 2010, 13 pages.

Gersbach, Marek et al., "A low-noise single-photon detector implemented in a 130 nm CMOS imaging process", Solid-State Electronics 53 (2009) 803-808.

Zappa, Franco et al., "Solid-state single-photon detectors", Optical Engineering, Society of Phot-Optical Instrumentation Engineers, vol. 35, No. 4, Apr. 1, 1996, pp. 938-945.

\* cited by examiner

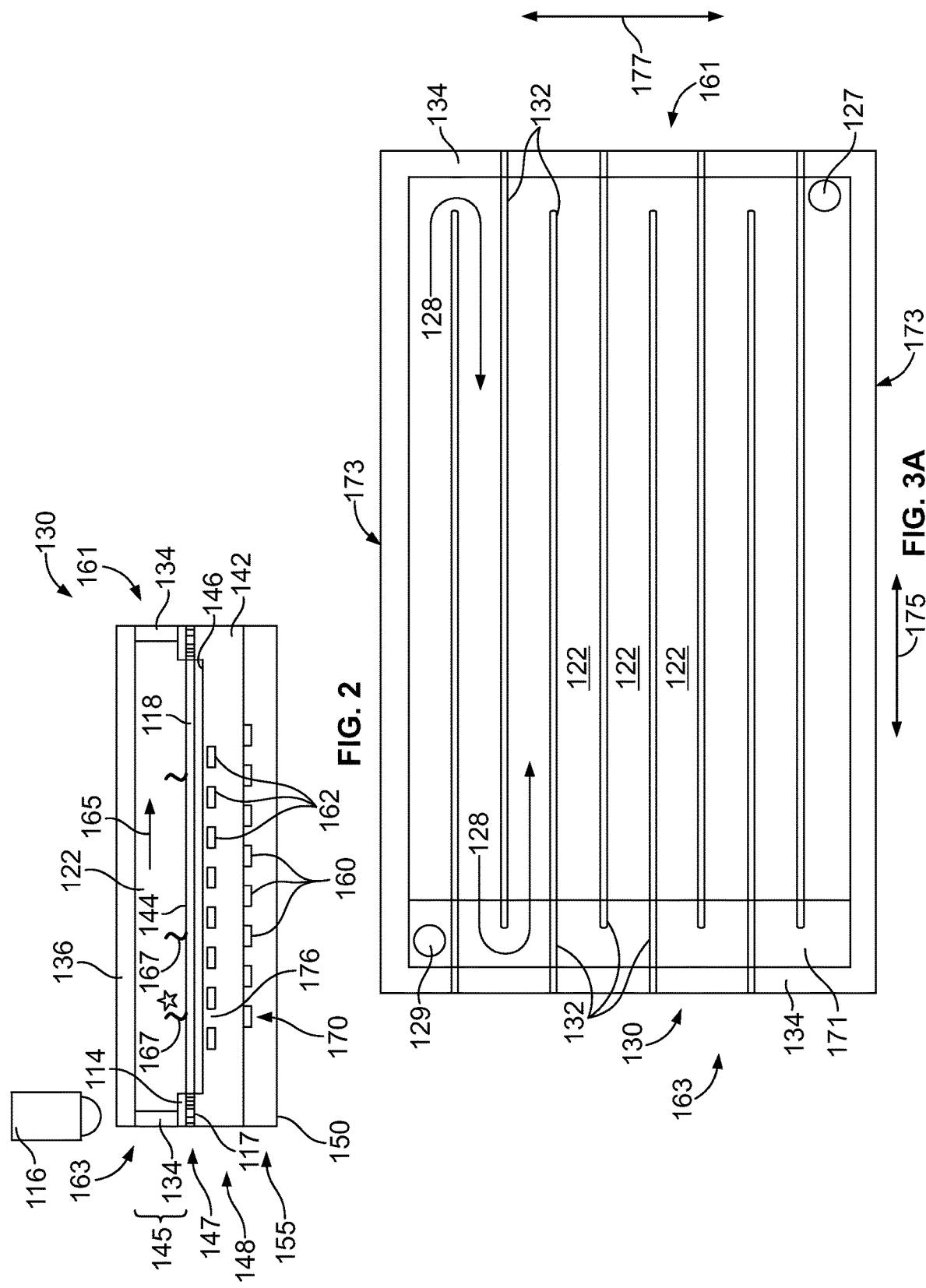

Photonic Light Circuit Elements

METHOD AND SYSTEM FOR FLUORESCENCE LIFETIME BASED SEQUENCING

CROSS REFERENCE TO RELATED APPLICATION

The present application is a National Stage Entry of International Application No. PCT/US2013/029837, filed Mar. 8, 2013 and entitled "METHOD AND SYSTEM FOR FLUORESCENCE LIFETIME BASED SEQUENCING," which claims the benefit of U.S. Provisional Application Ser. No. 61/684,984, filed Aug. 20, 2012 and entitled "METHOD AND SYSTEM FOR FLUORESCENCE LIFETIME BASED SEQUENCING," each of which is hereby incorporated by reference in its entirety.

BACKGROUND OF THE INVENTION

The subject matter herein relates generally to sequencing and more particularly to single molecule and cluster sequencing utilizing fluorescence chemistry and fluorescence lifetime decay information. The subject matter also relates to genotyping (e.g., bead chip technology) and more generally to fluorescence imaging to either measure lifetimes, or classify signals to one or more priori known species.

Various assay protocols exist for biological or chemical research that perform a large number of controlled reactions. In some cases, the controlled reactions are performed on support surfaces or within predefined reaction volumes. The controlled reactions may then be observed and analyzed to help identify properties or characteristics of the chemicals involved in the controlled reaction. For example, in some protocols, a chemical moiety that includes an identifiable label (e.g., fluorescent label) may selectively bind to another chemical moiety under controlled conditions. These chemical reactions may be observed by exciting the labels with radiation and detecting light emissions from the labels.

In some multiplex array-based assay protocols, populations of different probe molecules are immobilized to a substrate surface. The probes may be differentiated based on each probe's address on the substrate surface. For example, each population of probe molecules may have a known location (e.g., coordinates on a grid) on the substrate surface. The probe molecules are exposed to target analytes under controlled conditions such that a detectable change occurs at one or more addresses due to a specific interaction between a target analyte and the probe. For example, a fluorescently labeled target analyte that binds to a specific probe can be identified based on association of the fluorescent label with the address of the probe. The addresses on the array can be detected by an optical device to identify which populations reacted with the analytes. By knowing the chemical structure of the probe molecules that react with the analyte, properties of an analyte may be determined. In some multiplex assays, desired reactions are conducted on surfaces of individually identifiable microparticles that may also be scanned and analyzed. Many multiplex array-based assays are carried out in flow cells to facilitate repeated delivery of fluids carrying reagents useful for the assays. However, multiplex assays do not necessarily require repeated delivery of fluids and, thus, detection can be carried out on an open-face substrate without a flow cell.

An example of an assay protocol that can be carried out in an array-based protocol is sequencing-by-synthesis (SBS). In one SBS protocol, clusters of clonal nucleic acid amplicons are formed on a surface of a flow cell channel. After generating the clusters, the nucleic acid amplicons may be "linearized" to make single stranded nucleic acids, typically DNA (sstDNA). A series of reagents is flowed into the flow cell to complete a sequencing cycle. Each sequencing cycle extends the sstDNA by a single nucleotide (e.g., A, T, G, C) having a unique fluorescent label. In reversible terminator configurations, each nucleotide has a reversible terminator that allows only a single-base incorporation to occur at each sstDNA per cycle. After nucleotides are added to the sstDNAs clusters, an image in four channels is taken (i.e., one for each fluorescent label). After imaging, the fluorescent label and the terminator are chemically cleaved from the sstDNA and the growing DNA strand is ready for another cycle. Several cycles of reagent delivery and optical detection can be repeated to determine the sequences of the clonal amplicons.

Real-time single molecule sequencing has been demonstrated commercially, but is relatively challenging both from the chemistry perspective and from the sensor and illumination perspective. Also, the system implementations are complex and may not be optimal. The system complexity and sub-optimal set-up may be due, at least in part to the fact that real-time sequencing involves stochastic processes without a synchronized start and stop. Also, during real-time sequencing, the events have widely varying durations.

Further, certain types of reversible terminator-based SBS sequencing may be inherently slower than real-time sequencing methods due at least in part to the fluidic manipulations employed during each sequencing cycle. SBS is not mutually exclusive to real-time single-molecule sequencing. For example, in formats where the single molecule is not amplified, SBS chemistry can be run in free-running mode and thus, real-time. Traditional SBS systems typically require highly efficient filters to remove the excitation light. The SBS flow cells contain DNA molecules that are positioned on an unpatterned flow cell or a patterned flow cell. An unpatterned flow cell includes the DNA molecules located at random positions, whereas a patterned flow cell includes the DNA molecules located at predetermined positions on the flow cell.

Heretofore, temporal methods have been utilized to image assays for genotyping based on fluorescence lifetime measurements. Fluorescence lifetime based genotyping identifies fluorophores based on their fluorescence decay lifetime. Typically, a light source is pulsed to produce excitation pulses such that the excitation light is temporally separated from the fluorescence signal. In certain genotyping implementations, the pulsed excitation light may be further separated from the fluorescence signal through the use of spectral (or other) filters (can be polarization, etc.).

More recently, arrays of photon counters have been proposed in order to provide parallelized detection of multiple targets. The arrays of photon counters are formed on a silicon substrate using complementary metal oxide semiconductor (CMOS) technologies where each pixel element includes a single photon avalanche diode (SPAD).

However, CMOS SPAD arrays have experienced certain disadvantages.

A need remains for improved sequencing methods and systems.

BRIEF DESCRIPTION OF THE INVENTION

In accordance with one embodiment an integrated detection, flow cell and photonics (DFP) device is provided comprising: a substrate having an array of pixel elements that sense photons during active periods, the substrate and pixel elements forming an IC photon detection layer; at least one wave guide formed on the IC photo detection layer as a photonics layer, an optical isolation layer formed over at least a portion of the wave guide; and a collection of photo resist (PR) walls patterned to define at least one flow cell channel that is configured to direct fluid along a fluid flow path, the wave guides aligned to extend along the fluid flow path, the flow cell channel configured to receive samples at sample sites that align with the array of pixel elements.

The pixel elements include photon time of arrival (TOA) detector elements that continues one of an avalanche diode, a single photon avalanche diode, and a silicon photon multiplier. The device further comprising a grating optically coupled to an end of the waveguide, the isolation layer formed on the grating between the grating and the PR wall. The isolation layer is formed of silicon dioxide to decouple the waveguide from an outer wall that is formed above the waveguide.

The substrate constitutes a complementary metal oxide semiconductor (CMOS) substrate. The device further comprising a functionalization layer provided on the photonics layer, the functionalization layer configured to bond to samples. The IC photon detection layer includes a mask layer having an inter metal dielectric (IMD) substrate with at least one blocking layer embedded within the IMD substrate, the blocking layer having an array of mask apertures there through and aligned with the pixel elements.

The mask includes multiple opaque blocking layers stacked above one another and spaced apart by vertical gaps, the blocking layers having the mask apertures.

In accordance with an embodiment, an integrated detection, flow cell and photonics (DFP) device is provided that comprises; a flow cell channel defining a fluid flow path, the flow cell channel configured to hold samples at sample sites along the fluid flow path; a substrate having pixel elements formed therein to sense photons emitted from the samples during active sensing periods; a photonics layer for conveying excitation light to sample sites; an inter metal dielectric (IMD) layer formed on the substrate between the pixel elements and the flow cell channel, the IMD layer having a mask formed therein with mask apertures aligned with pixel elements and sample sites.

The mask includes mask apertures there through, the mask apertures having an optical collection geometry that has a parabolic cross-section as measured within a plane orientated perpendicular to the fluid flow direction. The flow cell channel extends in a longitudinal direction and has a lateral width, the mask apertures having a rectangular cross-section collection geometry in the longitudinal direction and a parabolic cross-section collection geometry in the lateral direction. The mask includes a collection of blocking layers stacked above one another and spaced apart by gaps in a direction of a depth of the IMD layer.

In accordance with an embodiment, an integrated detection, flow cell and photonics (DFP) device is provided that comprises a flow cell layer having flow cell channels that define a fluid flow path, the flow cell channels configured to hold samples in a sample pattern; a photonics layer, below the flow cell layer, configured to convey light along waveguides arranged proximate to the sample pattern; a detection layer, below the photonics layer, configured to detect photons emitted from the samples, the flow cell layer, photonics layer and detection layer being formed integral with one another; the detection layer including a substrate that includes an array of pixel elements, each of the pixel elements including an active area and an integrated circuit (IC) region within a boundary of the pixel element, the active area containing a photon time of arrival (TOA) detector element that senses photons during active sensing periods, the IC region including circuits to form start and end times for the active sensing periods, the IC region including a temporal accumulator to track time information associated with photons incident upon the photon TOA detector element relative to the active sensing periods; and the active areas being offset from centers of the corresponding pixel elements, the pixel elements being formed in the substrate to be adjacent to one another and clustered in sets such that the active areas for the pixel elements in one set are grouped proximate to one another in a cluster that is aligned with the fluid flow path through the flow cell channel.

The boundary of each pixel element is generally square or rectangular, the sets each include four pixel elements and the active area is formed in a corner of the pixel element such that the active areas in each set are located proximate to a center of the set. The boundary of each pixel element is generally square or rectangular and the active areas are formed proximate to an end of each pixel element, the sets of pixel elements being arranged in rows with the active areas aligned along an edge of the corresponding row and aligned with the fluid flow path through the flow cell channel, the IC regions being located remote from the edge.

In accordance with an embodiment, a method is provided for manufacturing an integrated detection, flow cell and photonics (DFP) device, comprising: forming a detection layer including a substrate that includes an array of pixel elements, each of the pixel elements including an active area and an integrated circuit (IC) region within a boundary of the pixel element; forming a photonics layer over the detection layer, the photonics layer configured to convey light along waveguides arranged proximate to the sample pattern; providing a functionalization layer over the photonics layer, the functionalization layer configured to bond to samples; providing an optical isolation layer over the functionalization layer to form a waveguide decoupling barrier; depositing and etching a first photoresist layer to form a sample site pattern through the isolation layer to expose the functionalization layer at sample sites; depositing a second photoresist layer over the optical isolation layer; and etching the second photoresist layer to form a flow cell layer having outer walls and flow cell walls formed of photoresist material, the outer walls, wherein at least the outer walls are separated from the photonics layer by the waveguide decoupling barrier.

Optionally, the active area contains a photon time of arrival (TOA) detector element that senses photons during active sensing periods, the IC region including circuits to form start and end times for the active sensing periods, the IC region including a temporal accumulator to track time information associated with photons incident upon the photon TOA detector element relative to the active sensing periods. The functionalization layer may represent a silicon nitride layer.

Optionally, the isolation layer represents a silicon dioxide layer. Optionally, the method comprising applying a hydroxysuccinimide (NHS) surface based on the zero background PEG (NHS-PEG) coating to the functionalization layer in the sample sites within the sample site pattern, and attaching samples to the NHS-PEG.

BRIEF DESCRIPTION OF THE DRAWINGS

FIG. 2 illustrates a side view of the DFP device formed in accordance with an embodiment.

FIG. 3A illustrates a top view of the DFP device of FIG. 1.

DETAILED DESCRIPTION OF THE INVENTION

Figure 1:
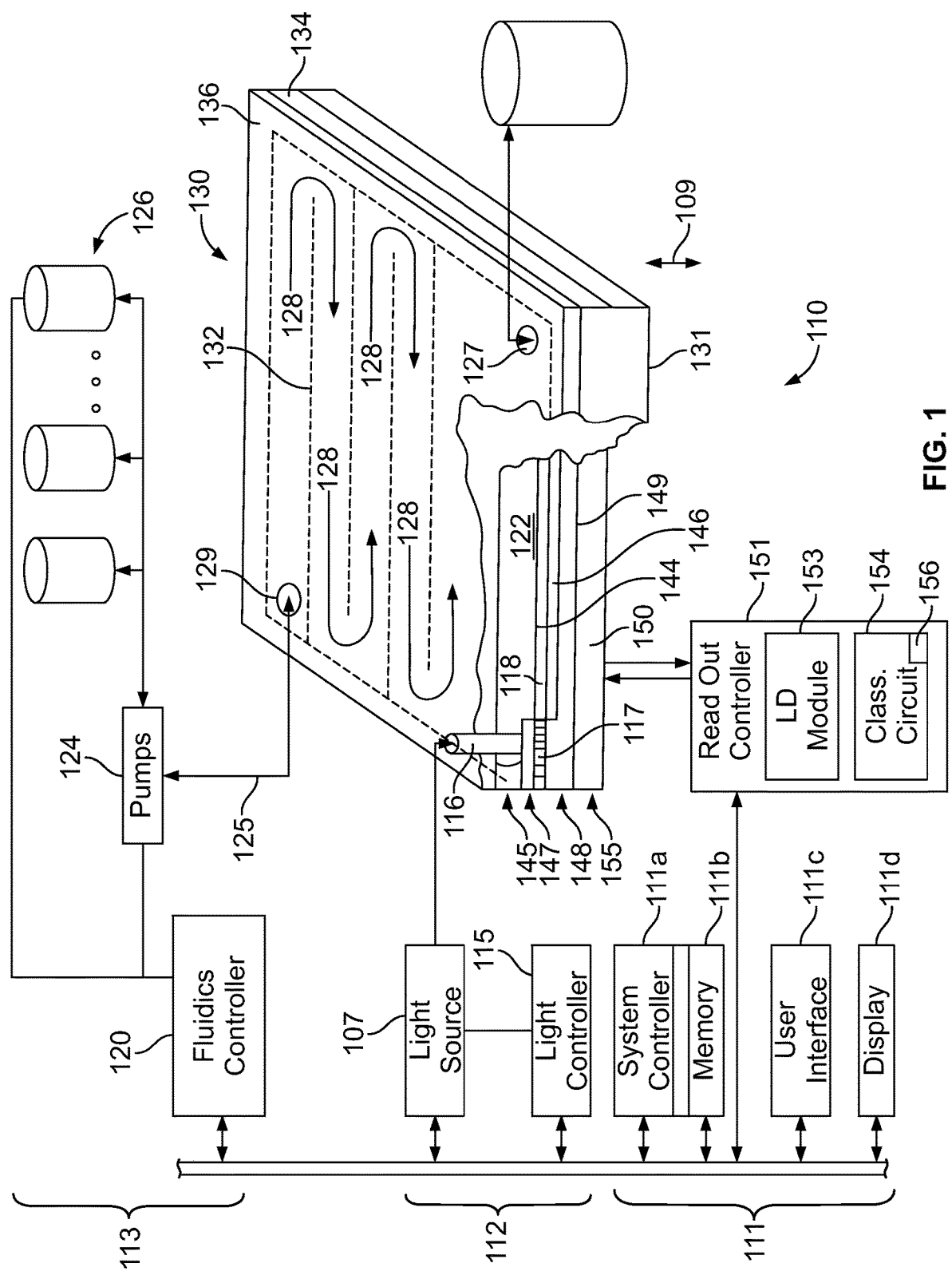
FIG. 1 is a block diagram of a system for biological or chemical analysis formed in accordance with one embodiment.

FIG. 1 illustrates a pictorial side view of a sequencing subsystem 110 formed in accordance with an embodiment. The sequencing subsystem 110 may be implemented within various systems such as the assay system 1000 discussed in connection with FIG. 9. The subsystem 110 includes a control sub-system 111, an excitation assembly 112, a fluidic assembly 113, and an integrated detection, flow cell and photonics (DFP) device 130. The control sub-system 111 includes a system controller 111a, memory 111b, a user interface 111c, and a display 111d.

The excitation assembly 112 excites samples on the DFP device 130. The DFP device 130 includes an integrated circuit (IC) photon detection layer 155 that includes integrated circuits that sense optical signals from the samples and outputs data signals indicative of label signatures associated with unique corresponding labels.

As used herein, the term "optical signals" includes electromagnetic energy capable of being detected. The term "optical signals" includes light emissions from labeled biological or chemical substances and also includes transmitted light that is refracted or reflected by optical substrates. The light emissions can be, for example, fluorescent emissions, luminescent emissions, or chemiluminescent emissions. For example, samples may include encoded microparticles that transform the incident light into optical signals that identify the microparticle (or substances immobilized on the microparticles). The transformed optical signals may form a detectable pattern that represents a code of the illuminated microparticle. Optical signals may also include incident light that is directed onto the sample to excite labels or to be reflected/refracted by the sample. Optical signals, including excitation radiation that is incident upon the sample and light emissions that are provided by the sample, may have one or more spectral patterns. More than one type of label may be excited at one point in time. For example, different types of labels may be excited by a common excitation light source or may be excited by different excitation light sources that simultaneously provide incident light. Each type of label may emit optical signals having a spectral pattern that is different from the spectral pattern of other labels. For example, the spectral patterns may have different lifetime decay patterns.

The sequencing subsystem 110 performs detection sessions in which all or a predetermined portion of the samples are detected. A detection session may be divided into multiple inspection frames. During each inspection frame, optical signals are detected from an associated set of samples. Each sample set may have a separate inspection frame. Each inspection frame comprises a series of active sensing periods (ASP) during which the IC photon detection layer 155 senses photons from aligned samples. In particular embodiments, a single ASP has a length of time that is defined such that there is a high probability that a single pixel element will encounter no more than one photon during the single ASP. For example, the ASP may be 10 nsec and the like. The length of the ASP is dependent upon the optical signal characteristics of the label being detected and the system noise.

An excitation pulse may precede each ASP, such as when the label is a fluorescent label. The excitation pulses can be timed between consecutive ASPs to excite the fluorescent labels.

One sample may undergo or be subject to multiple inspection frames which may or may not be overlapping in time. For example, one sample may be subject to two different inspection frames in which each inspection frame attempts to detect optical signals from one or more different labels. As a specific example, a first acquisition of a nucleic acid sample may detect labels associated with nucleotides A and C and a second acquisition of the sample may detect labels associated with nucleotides G and T. Optionally, a single acquisition may detect labels for nucleotides A, C, G and T. Different samples may be of the same type (e.g., two microarray chips) or of different types (e.g., a flow cell and a microarray chip). The acquisition can occur by scanning or other techniques as set forth below. One sample may contain multiple labels and the combined emission signal may be decomposed to reveal the identity of both samples.

During a detection session, optical signals emitted by the samples can be sensed by the IC photon detection layer 155. Various types of detection may be used with embodiments described herein. For example, embodiments may be configured to perform evanescent excitation via a waveguide. As explained hereafter waveguides are used for exciting the samples. Optionally, detection sessions may include detecting light emissions that are generated, without illumination, and based entirely on emission properties of a label within the sample (e.g., a radioactive or chemiluminescent component in the sample).

The DFP device 130 includes multiple functional layers that are stacked in a vertical direction 109 (also referred to as the depth of the DFP device 130). The functional layers include the photon detection layer 155, mask layer 148, a photonics layer 147 and a flow cell layer 145, all of which are formed integral with one another.

The flow cell layer 145 includes a photoresistive (PR) outer wall 134 that is formed about a perimeter of the DFP device 130. A lid 136 is provided over the PR outer wall 134. A series of PR channel walls 132 are provided between the base 131 and the lid 136. The channel walls 132 generally extend parallel to one another to define a series of flow cell channels 122. The channel walls 132 are staggered to form a serpentine fluid flow path 128 that wraps back and forth between a fluid inlet 129 and a fluid outlet 127. The fluid inlet 129 receives fluid from pump(s) 124 over a fluid conduit 125. The fluid 129 travels along the flow path 128, and is discharged at fluid outlet 127 to a discharge conduit 133 and discharge storage containers 135.

Optionally, the DFP 130 may include a single chamber surrounded by the PR outer wall 134, but without PR channel walls 132. Optionally, the DFP device 130 may be formed with a base, channel walls and an outer wall without utilizing a photo resistive process to form the walls. Instead, the base may have epoxy lines provided thereon. A lid may be provided with channel walls and an outer wall that are set onto the base along the epoxy lines. The lid has a bottom surface that is patterned to form the fluidic channels with the channel walls extending downward to the surface of the base.

The photon detection layer 155 includes a silicon substrate 150 with photon detectors formed therein. The mask layer 148 includes an inter-metal dielectric (IMD) substrate 142 (FIG. 2) formed on an upper surface 149 of the silicon substrate 150. The IMD substrate 142 has blocking plates or layers 162 (FIG. 2) therein. The mask layer 148 also includes a passivation or cladding layer 146 that is provided on an upper surface of the IMD substrate 142.

The photonics layer 147 includes a series of waveguides 118. Planar light structures, such as gratings, beam splitters, channel waveguides, are formed directly on an upper surface of the passivation layer 146, thereby directly forming the photonic layer 147 on the passivation layer 146 (e.g., a glass layer). The waveguide portion of the planar light structures can either be a monolithic plane (planar waveguides) or patterned to form multiple channel waveguides. In the latter case, higher energy density may be achieved with the same input power. The waveguides 118 have upper surfaces that are covered with a functionalization layer 144 which includes samples 167 bound thereto. For example, the functionalization layer 144 may represent a silicon nitride layer or other type of layer that binds to samples and does not cause propagation loss in the waveguide 118. The functionalization layer 144 extends along the floor or bottom in the flowcell channels 122. The functionalization layer 144 is configured to receive and retain samples throughout a sequencing cycle as various reagents are processed through the fluid flow path 128. The photonics layer 147 also includes optical isolation or decoupling borders 114 (e.g. made of silicon dioxide, SiO2) formed over the functionalization layer 144 at the outer walls 134.

Certain areas of the waveguide (also referred to as a Photonic Light Circuit because it includes other circuit elements such as gratings, focused grating, beam splitter of various kinds, turns and terminations) may be coated with a capping layer to isolate the propagating field from the environment. Such capping layer is typically thicker than several times of the penetration depth of the evanescent field. For example, a capping layer, e.g., SiO2, may be formed on the periphery of the waveguide layer to allow for application of an epoxy without causing optical losses. Similarly, the capping layer may be formed above the waveguides and below the fluidic channel walls. Thin films, such as of silicon nitride, tantalum pentoxide, with a thickness substantially smaller than the mode diameter of the propagating beam may be deposited on top of the waveguide structure, for example, to chemically seal the waveguides and underlying circuitry from contaminants. Similarly such thin films of organic molecules may be deposited and patterned to allow for attachment of DNA molecules onto specific locations on the surface of the die, e.g., right above the active area of the sensing elements such as to maximize the geometrical collection efficiency of emitted photons.

Light scattering out of the waveguides, gratings and other circuit elements can interfere with the operation of the electronic circuitry underneath the waveguides since light is in the visible wavelength, unlike in communication-wavelength waveguides. A sufficiently opaque layer, (e.g., metal) may be laid out underneath the planar light circuit elements but sufficiently far away as to not interfere with the propagating field (several penetration lengths) in order to reflect or absorb this scattered light.

The fluidic assembly 113 includes a fluidic controller 120 that controls one or more pumps 124 that manage the supply of new reagent fluid from a collection of new reagent containers 126. Select amounts of reagents from the containers 126 are passed through an inlet fluid conduit 125 to a fluid inlet 129 in accordance with a sequencing protocol.

The excitation assembly 112 includes a light source 107, such as a laser beam and the like, that generates one or more pulsed beams of light at one or more light introducers 116. The gratings 117, in the excitation assembly 112, changes the propagation of a part of the laser beam as well as its shape such that it is directed onto the thin waveguide layer. One or more splitters separate the light beam from the introducer 116 into multiple light beams. As one example, a single light beam from an introducer 116 may be directed onto a grating 117 which then redirects the light into a single wide channel waveguide. A mode converter gradually narrows the beam diameter and feeds the beam into a narrow channel waveguide. A splitter subsequently splits the light uniformly into a plurality of waveguides 118. For example, a single light beam may be split by multiple stages of splitters into four or more optical paths that are then redirected into four or more waveguides 118. Optionally, a separate introducer 116 along with a grating coupler may be provided for each waveguide 118.

The waveguides 118 are arranged in a desired pattern, such as a series of parallel linear paths in a two dimensional array, based on the layout of the flow cell channels 132. The light source 107, mechanical alignment stage (required especially for 2 wavelengths because the coupling angles for the 2 wavelengths are different) and the waveguides 118 output the light at wavelengths (e.g., 532 nm and 660 nm) that correspond to the excitation wavelengths of corresponding labels (e.g., fluorophores). At the beginning of an ASP, a pulse may be output from each introducer 116 at a first wavelength and first direction that corresponds to the excitation wavelength of a first fluorophore. During the next ASP, a pulse may be output from each introducer 116 at a second wavelength and from a second direction that corresponds to the excitation wavelength of a second fluorophore. This process may be repeated for multiple different wavelengths. Optionally, each pulse may include all wavelengths of light necessary to excite all possible fluorophores. An active alignment scheme comprised of the light source, mechanical alignment stage, waveguides and imager array. In order to find the optimal coupling angle the laser is fired, propagating light through the waveguides. Some of this light leaks from the waveguides and is collected by the underlying pixels. Alternately, a fluorescence signal from excited fluorophores is collected. The intensity of leaked light is recorded. The coupling angle and/or location of incident beam is changed by a controller through the mechanical stage using a search algorithm until a coupling angle which results in maximum scattered light out of the channels is found. Because the scattered intensity correlates with the propagating light intensity, this is the optimal coupling angle. Alternately, a grating is placed at the far end of the waveguide, coupling the light either out of the imager into an external camera or into sensor elements on the die, and, as before, an optimal coupling angle is found when the light intensity is maximal.

The light source 107 is controlled by an excitation controller 115 that directs the light source 107 to generate light pulses at predetermined pulse widths during a detection session. For example, the pulse width may be comparable or shorter than a shortest decay lifetime for any of the fluorophores used for labeling. Each light pulse is timed to correspond to the beginning of a corresponding ASP within a detection session. By way of example, the excitation controller 115 may use pulsed excitation that is defined based on a priori knowledge of fluorophorelifetimes that are to be excited. The IC photon detection layer 155 then processes those photons that arrive within an expected window, and thus resolve non-correlated photons (e.g., leakage from the waveguides or free-floating dyes in solution) or non-correlated noise (e.g., dark noise or ambient light).

Optionally, the excitation assembly 112 may include a waveguide excitation conduit, such as described in PCT Publication WO 2006/111729, "Method and Device for Nucleic Acid Sequencing using a Planar Wave Guide", published Oct. 26, 2006, the complete subject matter of which is expressly incorporated herein by reference, or, more specifically by an array of channel waveguides. Excitation occurs via the channel waveguide 118 into the flowcell channels 122. The functionalization layer is in contact with the reagents. The excitation assembly 112 may utilize the scheme that is described in the WO '729 application. A waveguide excitation scheme may be particularly useful for real time single molecule imaging because the excitation volume under waveguide illumination can be confined within hundreds of nanometers from the waveguide core, thus reduces unwanted detection of free floating nucleotides (non-correlated photons). More specifically, a channel waveguide excitation scheme generates a lower overall number of unwanted non-correlated photons for a given array if the waveguide channels are aligned to the location of the biomolecules because the regions between such lanes of molecules are not illuminated. For example, in a real-time system, a separate washing step may not be available to remove unincorporated nucleotides. In both a planar and channel waveguide schemes, excitation is achieved via an evanescent field, whose effect diminishes over a very small distance. Thus, nucleotides which do not actually reside on the surface, such as unincorporated nucleotides, will not get excited.

FIG. 2 illustrates a side view of the DFP device 130 formed in accordance with an embodiment. The DFP device 130 includes opposed ends 161 and 163, between which fluid flows in the flow cell channel 122 that is illustrated with a fluid flow direction 165 extending from left to right across the page. The DFP device 130 includes a stacked arrangement, from the bottom up, that includes the silicon substrate 150, IMD substrate 142, passivation layer 146, waveguide 118, functionalization layer 144, decoupling border 114, outer walls 134, flowcell channel 122 and lid 136. The PR outer walls 134 are provided along the ends 161 and 163. The gratings 117 are provided at opposite ends of the waveguide 118 to manage the light within the waveguide 118 in a manner as described herein.

The substrate 150 includes integrated circuits that form an array of "tixels" (time-domain picture elements) 160. In an exemplary embodiment, the substrate 158 may be a silicon substrate and have in-pixel CMOS circuitry forming the tixels to distinguish or identify one or more fluorophores in parallel, based on the fluorescence lifetimes of the fluorophores. The tixels 160 each measure cumulative information relating to the statistics of photon time arrivals over a multitude of photon arrivals at each corresponding tixel 160. The tixels 160 measure the average time of arrival of photons with respect to the excitation source with relatively good precision (e.g., 0.5 to 1 nsec).

The tixels 160 measure average time of arrival, not cumulative time of arrival. By using average time of arrival, the tixels 160 do not need uniform photon arrival. When measuring cumulative time of arrival, the system becomes more dependent on uniform photon arrival (and thus requires uniform fluorescence intensity which is not readily attainable with single photon emissions). However, by measuring average time of arrival, the tixels 160 work well even when photon arrival is non-uniform (e.g. stochastic), and thus does not require uniform fluorescence intensity and operates well with single photon emissions.

As shown in FIG. 2, an opaque blocking layer 162 is provided within the IMD layer 148. The blocking layer 162 may be a guard ring that covers the non-active areas to reduce undesired photon absorption which will result in higher jitter. For example, the tixels 160 may utilize avalanche diodes, single photon avalanche diodes, silicon photo multipliers or other detectors that have good precision in measuring TOA. The blocking layer 162 may have multiple blocking layers such as metal coatings that cover all areas outside of the tixels 160 and blocks photons from reaching the substrate 150. The blocking layer 162 represents a mask that includes mask apertures 176 therethrough. The mask apertures 176 overlay and align with the tixels 160. Each tixel 160 and mask aperture 176 collectively form a corresponding pixel element 170 (also referred to as photon TOA detector element). In an exemplary embodiment, the substrate 158 may be a CMOS substrate and have in-pixel circuitry to identify one or more fluorophores in parallel, based on the fluorescence lifetimes of the fluorophores.

The arrangement of the apertures in the metal layers can be made to follow the contours of a paraboloid, which maximizes collection efficiency of light originated from the focus of the parabola. The metal aperture stack may be asymmetric along two orthogonal directions. For example, the metal aperture stack can be parabolic in the cross section along the direction perpendicular to the fluidic flow direction, while it can be a parallel tunnel along the direction of fluidic flow. The metal aperture stack follows the expected geometry of emissions, such as when emission is expected from a long strand of DNA stretched in a preferential direction by a fluidic flow (e.g., parallel to the direction of the channel waveguide). The waveguide may be patterned with periodic structures such as a photonic crystal to better guide the light. A defect in the periodic structure may be lithographically or otherwise created above the active pixel area such that light leakage from the waveguide is maximized in those locations thus maximizing the excitation intensity in predetermined regions. The following article describes examples of systems and methods that implement defects within waveguides to achieve a desired light leakage characteristic: Light Localizations in Photonic Crystal Light Defect Waveguides, Toshihiko Baba et al., IEE Journal of Selected Topics in Quantum Electroncis, Vol. 10, No. 3, May/June 2004. The complete subject matter of the above Baba et al. article is expressly incorporated herein by reference in its entirety.

The functionalization layer 144 has samples 167 bound at sample sites. As used herein, the term "sample" includes various matters of interest that undergo a detection session where optical signals from the sample are observed. In particular embodiments, a sample may include biological or chemical substances of interests and, optionally, an optical substrate or support structure that supports the biological or chemical substances. As such, a sample may or may not include an optical substrate or support structure. As used herein, the term "biological or chemical substances" may include a variety of biological or chemical substances that are suitable for being detected or examined with the optical systems described herein. For example, biological or chemical substances include biomolecules, such as nucleosides, nucleic acids, polynucleotides, oligonucleotides, proteins, enzymes (such as ligase or polymerase), polypeptides, antibodies, antigens, ligands, receptors, polysaccharides, carbohydrates, polyphosphates, nanopores, organelles, lipid layers, cells, tissues, organisms, and biologically active chemical compound(s) such as analogs or mimetics of the aforementioned species. Biological or chemical substances can include labels that can be used for identification, examples of which include fluorescent labels and others set forth in further detail below. Such labels can be associated with biological or chemical substances, for example, by covalent attachment, affinity interactions, ionic interactions, van der Waals interactions, hydrogen bonding or a combination thereof.

Different types of samples may include different optical substrates or support structures that affect incident light in different manners. In particular embodiments, samples to be detected can be attached to one or more surfaces of a substrate or support structure. For example, open-face substrates (such as some microarrays and chips) can have biological or chemical substances immobilized to an exterior surface of the open-face substrate. As such, optical signals to be detected are projected from an exterior surface through air and perhaps through liquid having different indices of refraction when the optical signals are collected from above. However, flow cells or capillary flow optical substrates may include one or more flow channels. In flow cells, the flow channels may be separated from the surrounding environment by top and bottom layers of the flow cell. Thus, optical signals to be detected are projected from within the support structure and may transmit through multiple layers of material having different refractive indices. For example, when detecting optical signals from an inner bottom surface of a flow channel and when detecting optical signals from above the flow channel, the optical signals that are desired to be detected may propagate through a fluid having an index of refraction, through one or more layers of the flow cells having different indices of refraction, and through the ambient environment having a different index of refraction. Accordingly, the optical signals propagating from the open-face substrate may be affected differently than the optical signals propagating from a surface of the flow channel.

Different types of optical substrates or solid support structures used in a method, system, or apparatus set forth herein can have various compositions and properties. Substrates and support structures can differ from each other with regard to, for example, type of material (e.g., glass, plastic), a thickness of the solid material, spacing of a gap between solid material layers, number of solid material layers in which the solid material layers may comprise the same or different materials, number of gaps between solid material layers, chemical nature of gases or liquids in contact with one or more solid material layers, refractive index of the solid material, refractive index of liquid in contact with a solid material layer, and the like. In some embodiments, the optical substrate may include a gel that supports the biological substances and permits optical signals to transmit there through.

Optical substrates or support structures include flow cells having flow channels where, for example, nucleic acids are sequenced. In other embodiments, optical substrates may include one or more slides, open-face substrates or planar chips (such as those used in microarrays), or microparticles. In such cases where the optical substrate includes a plurality of microparticles that support the biological or chemical substances, the microparticles may be held by another optical substrate, such as a slide, array of pits, or grooved plate. In particular embodiments, the optical substrate includes diffraction grating based encoded optical identification elements similar to or the same as those described in pending U.S. patent application Ser. No. 10/661,234, entitled Diffraction Grating Based Optical Identification Element, filed Sep. 12, 2003, which is incorporated herein by reference in its entirety, discussed more hereinafter. A bead cell or plate for holding the optical identification elements may be similar to or the same as that described in pending U.S. patent application Ser. No. 10/661,836, entitled "Method and Apparatus for Aligning Microbeads in Order to Interrogate the Same", filed Sep. 12, 2003, and U.S. Pat. No. 7,164,533, entitled "Hybrid Random Bead/Chip Based Microarray", issued Jan. 16, 2007, as well as US patent applications, Ser. No. 60/609,583, entitled "Improved Method and Apparatus for Aligning Microbeads in Order to Interrogate the Same", filed Sep. 13, 2004, Ser. No. 60/610,910, entitled "Method and Apparatus for Aligning Microbeads in Order to Interrogate the Same", filed Sep. 17, 2004, each of which is incorporated herein by reference in its entirety. The substrate may also be the top face of the CMOS imager chip, possibly after it has been sufficiently polished and/or chemically functionalized.

FIG. 3A illustrates a top view of the DFP device 130 of FIG. 1. The DFP device 130 includes ends 161 and 163, and sides 173. The DFP device 130 is elongated in a rectangular configuration to have a longitudinal dimension 175 and a lateral dimension 177. The flow cell channels 122 are oriented such that fluid flows substantially parallel to the longitudinal dimension 175 and wraps between channels 122 at the ends 161 and 163. Similarly, the waveguides 118 are oriented to extend parallel to the longitudinal dimension 175 and may be centered within the flow cell channels 122. As shown in FIG. 3A, the DFP device 130 includes an exemplary fluid flow path 128 that travels from the fluid inlet 129 to the fluid outlet 127. The channel walls 132 are oriented parallel to one another but are staggered such that one end of each channel wall 132 engages (e.g., may be formed with) the outer wall 134 while the opposite end of each channel wall 132 stops short of the outer wall 134 to form a gap 171 between adjacent flowcell channels 122.

Figure 3B:
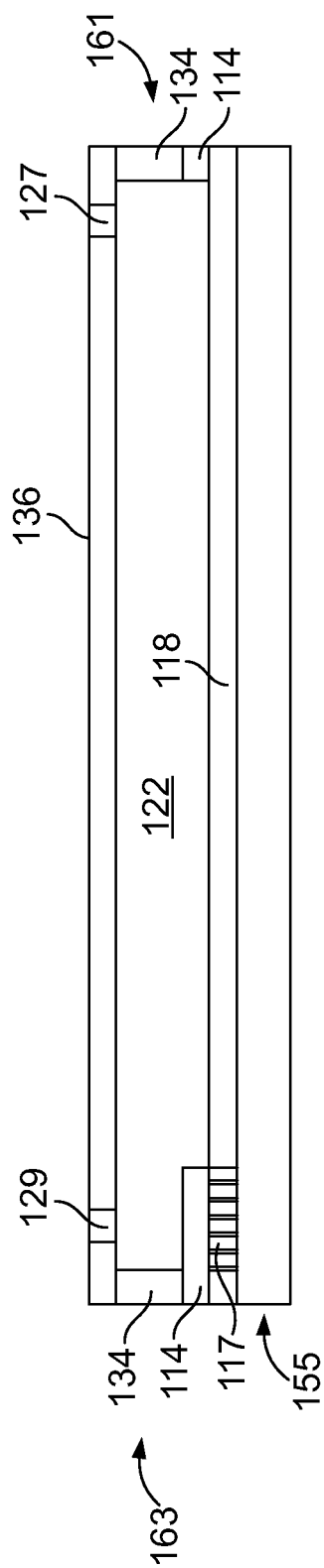
FIGS. 3B and 3C illustrate a side and end view, respectively, of the DFP device of FIG. 1.
Figure 3C:
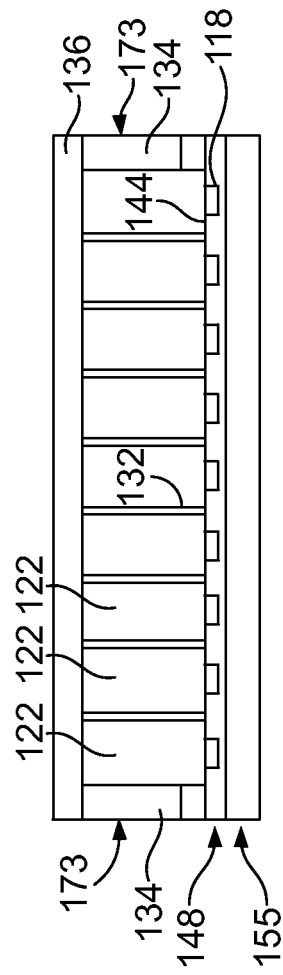

In the example of FIGS. 3A-3C, the flow cell channels 122 are oriented to extend along a longitudinal length of the DFP device 130. Optionally, the flow cell channels 122 may be oriented to extend along a lateral width of the DFP device 130. Although the pattern of flow cell channels 122 is exemplified as a rectilinear pattern, it will be understood that other patterns can be used including, but not limited to, a spiral pattern, a non-rectilinear pattern such as a hexagonal pattern, and the like.

While not shown in FIGS. 3A-3C, it is understood that an array of pixels 170 is distributed across the DFP device 130. For example, pixel elements 170 may be provided in rows that extend generally along a central axis of each of the flow cell channels 122. FIGS. 3B and 3C illustrate side and end views, respectively, of the DFP device 130. FIG. 3B illustrates the ends 161 and 163 of the outer wall 134, while FIG. 3C illustrates the sides 173 of the outer wall 134. FIG. 3B illustrates the waveguide 118 extending along a length of a flow cell channel 122, while FIG. 3C illustrates ends of a series of flow cell channels 122.

As shown in FIG. 3B, the optical decoupling of isolation border 114 is provided on the outer edges of the waveguide 118. The isolation border 114 may be formed from silicon di-oxide (SiO2) or another similar type of material that has a substantially lower refractive index than the core material of the waveguide 118. The isolation border 114 is provided between the edges of the waveguide 118 and the PR outer walls 134 to optically separate and isolate the PR outer walls 134 from the waveguide 118. The isolation border 114 covers any portions of the waveguides 118 that are located below the outer walls 134. For example, the isolation border 114 extends along the ends 161 and 163 (FIG. 3A). Optionally, the border 114 may also be located between each channel wall 132 and the functionalization layer 144.

Figure 3E:
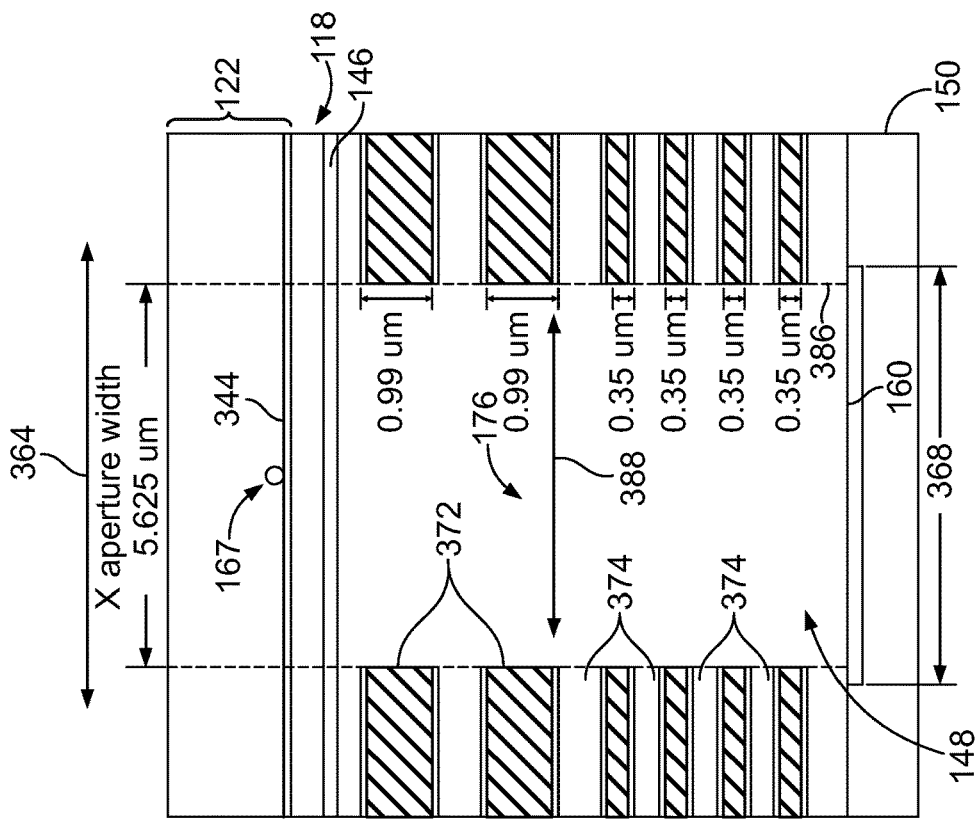
FIGS. 3D and 3E illustrate end and side views, respectively, of a cut-out portion of a DFP device associated with a single pixel formed in accordance with an embodiment.
Figure 3D:
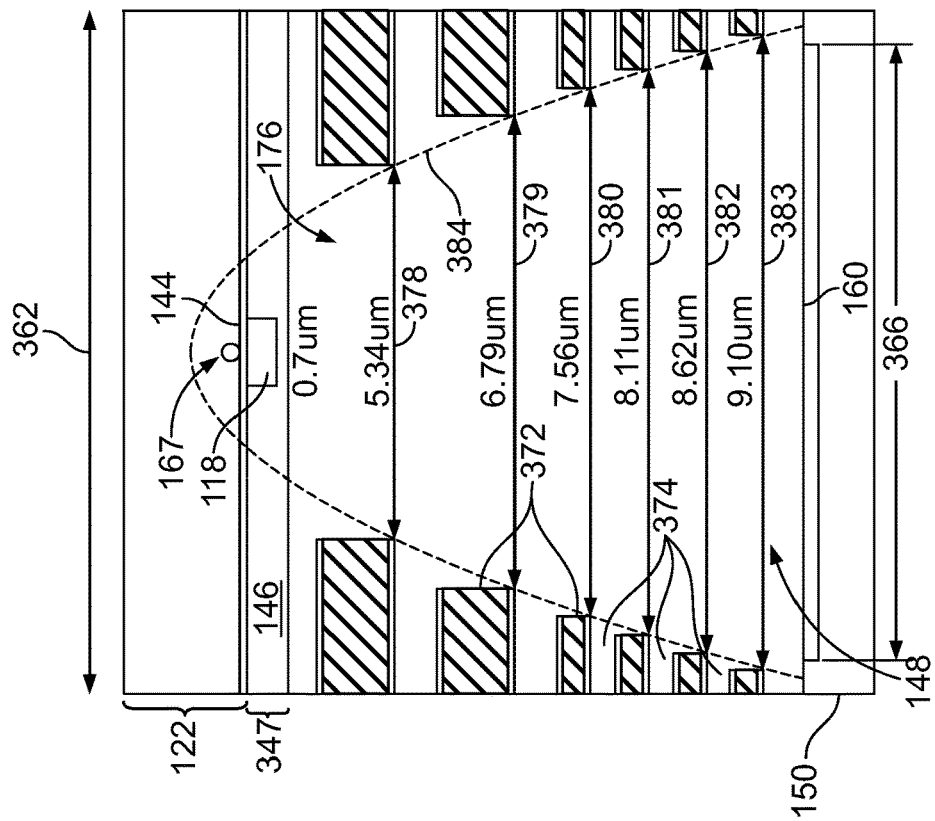

FIGS. 3D and 3E illustrate end and side views, respectively, of a cut-out portion of a DFP device associated with a single pixel 370 formed in accordance with an embodiment (e.g., which may correspond to a single pixel 170 in FIG. 1). The side view of FIG. 3E illustrates a portion of a cross-section of pixel 370 where the cross-section plane extends along a longitudinal direction 364 that corresponds to (and is parallel to) the longitudinal dimension 175 (FIG. 3A) and the length of the flow cell channels 122. The end view of FIG. 3D illustrates a cross-section of a portion of a pixel 370 where the cross-section plane extends along a lateral direction 362 that corresponds to (and is parallel to) the lateral dimension 177 (FIG. 3A) and the width of the flow cell channels 122.

The end view of FIG. 3D is oriented to view an end of a single waveguide 118 such that the waveguide 118 extends into the page. The pixel 370 includes a tixel 160 provided in the substrate 150, below a mask layer 148. The mask layer 148 is located below the wave guide 118. The waveguide 118 is located below the flow cell channel 122 which includes a single sample 167 secured to the functionalization layer 144.

The mask layer 148 includes the IMD substrate 142 having embedded therein a collection of metal layers 372 that are stacked upon one another, but spaced apart from one another by gaps 374 filled with an inter-metal dielectric (e.g. silicon dioxide). The metal layers 372 collectively block light from impinging upon the electronics in the DFP device, blocks light from one pixel reaching other pixels and blocks some of the light from free floating dyes or from waveguide scattering and autofluorescence from reaching the SPAD active area. The metal layers 372 have mask apertures 176. The mask apertures 176 are aligned with tixels 160 and locations at which samples 167 are secured to the functionalization layer 144. The mask apertures 176 have different sizes in each of the metal layers 372 to collectively form a collection geometry that directs emission from the sample 167 onto the corresponding tixel 160. As illustrated in FIG. 3D, the mask aperture 176 is defined by a series of openings through the metal layers 372, where each opening has a progressively larger widths 378-383 beginning at the metal layer 372 closest to the sample 167 and ending at the metal layer 372 closest to the tixel 160. The widths 378-383 of the openings through the metal layers 372 are dimensioned and spaced apart from one another to form a generally parabolic opening 384 cross-section denoted by a dashed line which has a peak proximate to sample 167 and a base at outer edges of the tixel 160. The openings through the metal layers 372 are dimensioned such that the parabolic opening 384 is provided at each sample 167 along the length of the waveguide 118. The parabolic opening 384 is oriented to be substantially perpendicular to the length of the waveguide 118 to facilitate directing as much emission as practical from the sample 167 onto the corresponding tixel 160. Stated another way, the mask aperture 176 has a parabolic shape (as denoted at 384) when measured in the lateral direction 362. The parabolic cross-section is measured within a plane oriented perpendicular to the fluid flow direction.

Turning to FIG. 3E, the mask aperture 176 has a generally rectangular cross-section collection geometry as denoted at 386 when measured in the longitudinal direction 364 that is parallel to the fluid flow direction. As shown in FIG. 3E, the openings through the metal layers 372 have substantially equal widths 388 as measured in the longitudinal direction 364 which is parallel to the length of the waveguide 118.

As shown in FIGS. 3D and 3E, the tixel 160 may have an active area with a rectangular shape having an active aperture width 368 (FIG. 3E) and an active aperture height 366 (FIG. 3D). FIGS. 3D and 3E illustrate exemplary widths 388 and 378-383 for the openings through the metal layers 372.

As explained above, the openings through the metal layers 372 form parabolic collection geometry as measured in a lateral direction perpendicular to the length of the waveguides 118 and also measured in the direction of fluid flow. The openings through the metal layers 372 form a rectangular collection geometry as measured in a longitudinal direction parallel to the length of the waveguides 118 and also measured laterally/perpendicular to the direction of fluid flow. As one example, the samples 167 may target long DNA strands where the distance between bases is 3-4 angstroms. As fluid flows along the flow cell channel 122, the DNA strands may "bend" in the direction of fluid flow (parallel to fluid flow and to the length of the flow cell channel 122). The above collection geometry is configured to afford good optical coupling to the light emitted from the sample 167 given that the samples 167 may "bend" in the direction of fluid flow.

The geometry of the mask apertures 176 may be formed from elongated holes or spheres in each of the metal layers 372. The geometry of the mask apertures 176 is oriented with respect to the direction of fluid flow which corresponds to a direction in which the samples will be tilted or bent.

As shown in FIGS. 3D and 3E, the passivation layer 146 is provided above the mask layer 148, and between the mask layer 148 and the waveguide 118 and the flow cell channel 122. The thickness 347 of the passivation layer 146 is sufficient to provide a desired spacing between the uppermost metal layer 372 and the waveguide 118 and the flow cell channel 122. The desired spacing between the uppermost metal layer 372 and the waveguide 118 and the flow cell channel 122 prevents (or at least substantially limits) light propagation losses that might otherwise be caused by the metal layers 372.

The metal layers 372 block light from impinging upon the active electronic elements in the silicon substrate.

Figure 3F:
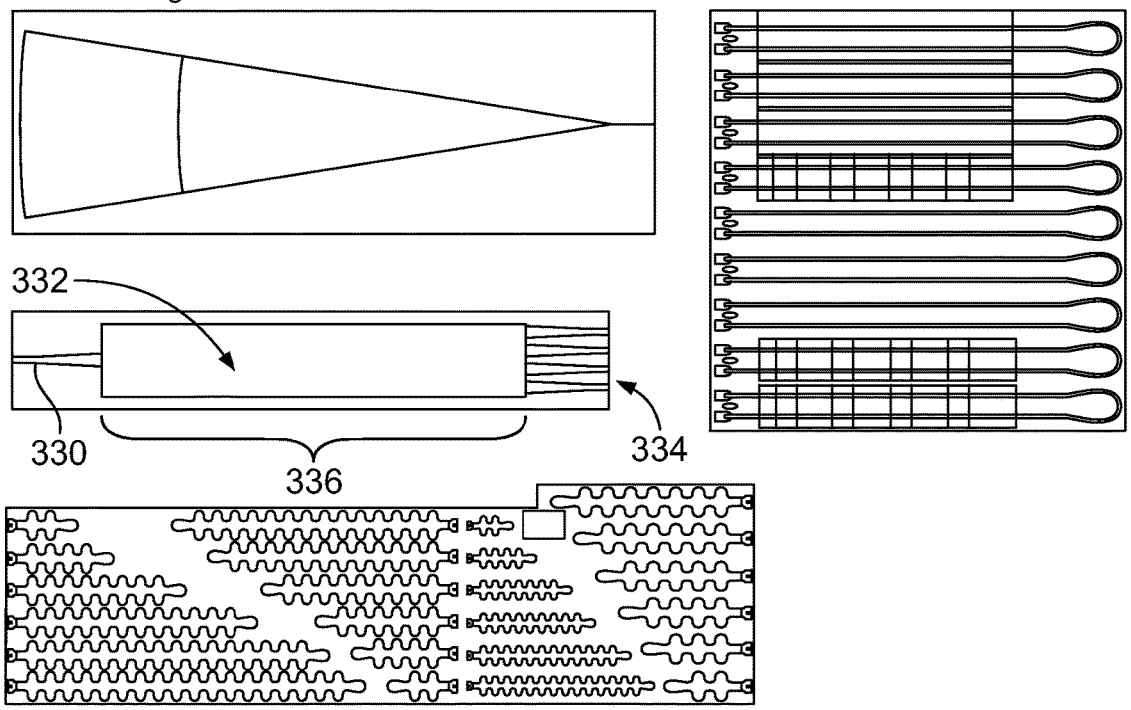
FIG. 3F illustrates a functional view of a portion of the grating of FIGS. 2 and 3A that is provided at one end of a group of adjacent waveguides.

FIG. 3F illustrates a functional view of various planar photonics structures, such as grating coupler 117 (FIGS. 2 and 3A) that is provided at one end of a group of adjacent waveguides 118 (top left graph). The middle left graph illustrate one type of beam splitters in a planar format. The planar beam splitter includes a light inlet 330 that is optically coupled to the grating coupler 117 (FIG. 2). The grating 117 couples light into a region that represents an optical splitter 332 that split the light into multiple beams that are output at light outlets 334. The light outlets 334 are each optically coupled to an upstream end of a corresponding channel waveguide 118. The optical splitter 332 has a short depth 336 dimension to afford a space efficient structure to be located in, without unduly extending the overall size of, the DFP device 130.

Figure 3G:
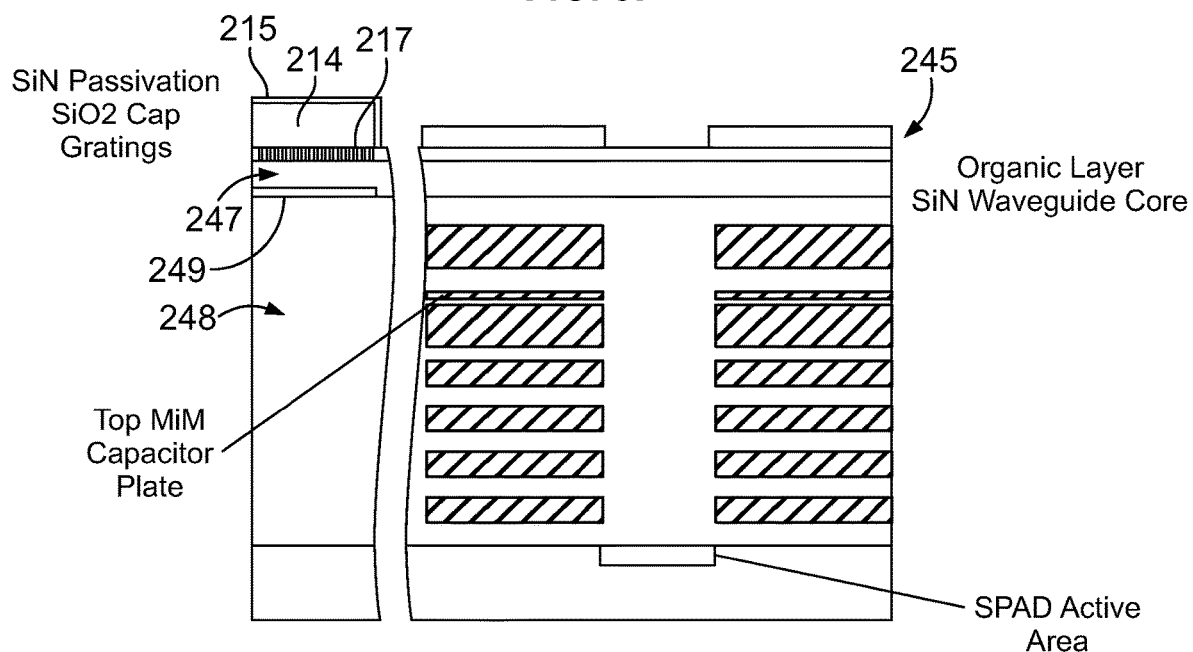
FIG. 3G illustrates a portion of a DFP device formed in accordance with an alternative embodiment.

FIG. 3G illustrates a portion of a DFP device 230 formed in accordance with an alternative embodiment. The DFP device 230 includes the IC photon detection layer 255, mask layer 248, a photonics layer 247 and a flow cell layer 245, all of which are formed integral with one another. Gratings 217 are provided at the end of the photonics layer 247, with a decoupling border 214 and a Silicon Nitride passivation layer 215 provided over the gratings 217.

Figure 3H:
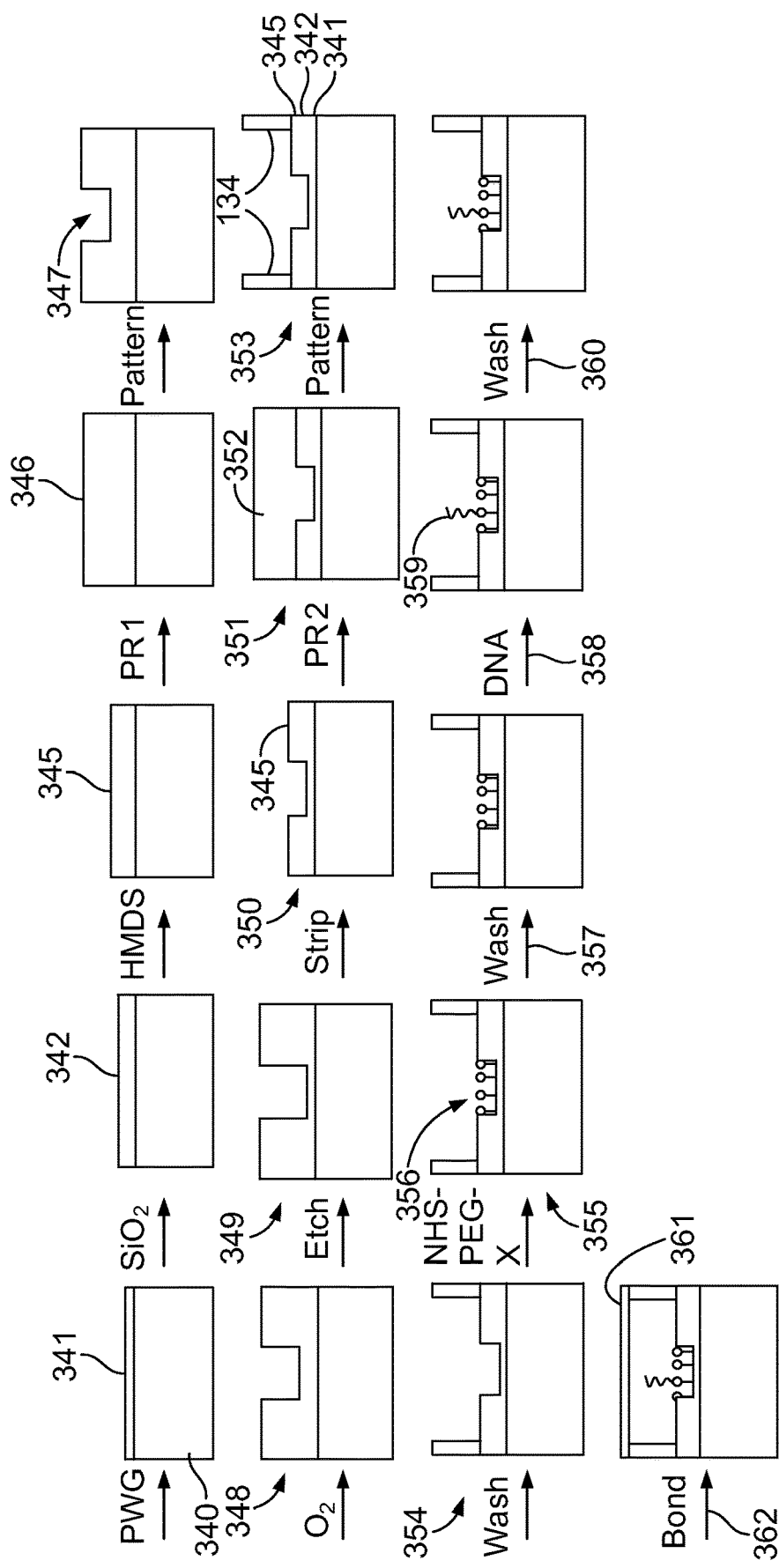
FIG. 3H illustrates a process for forming a wafer-scale flow cell in accordance with an embodiment.

A thin metal reflection layer 249 is provided between the photonics layer 247 and the mask layer 248. The reflection layer 249 is located below the gratings 217 to prevent light that may escape from the gratings 217, from traveling into the mask layer 248. The reflection layer 249 may extend along an end of the DFP 230 in substantially the same pattern as the decoupling border 214. FIG. 3H illustrates a process for forming a wafer-scale flow cell in accordance with an embodiment. The process begins with a silicon wafer and waveguide 340. Next, a silicon nitride layer 341 ($Si_xN_y$) is deposited over the planar waveguide 340 (e.g. 5-10 nanometers thick). The SiN layer 341 forms the functionalization layer 144 to which samples bond. The SiN layer 341 prevents contaminants from diffusing to the waveguide and underlying circuitry. Next a silicon dioxide (SiO2) layer 342 (e.g., 5-10 nanometers) is deposited. The SiO2 layer 342 prevents light from propagating out of the waveguide 340. Next an HMDS layer 345 is deposited over the SiO2 layer 342, and a photoresist layer 346 is deposited over the HMDS layer 345. A pattern is formed in the photoresist layer 346 such as by forming a hole 347 in the photoresist layer 346 directly above the active area in the pixel.

Oxygen plasma etch is used to remove the HMDS within the hole 347 (at 348), followed by etching to remove the SiO2 portion aligned with the hole 347 (at 349). Next, a remainder of the photoresist layer 346 is removed or stripped to expose the HMDS 345 (denoted at stage 350). The SiN layer 341 remains throughout the above processes and is now exposed in the hole 347. In one implementation, at 351, a second photoresist layer 352 is deposited and then patterned by etching at 353. The pattern formed by etching at 353 creates the PR outer walls 134 and PR channel walls 132 described above in connection with FIGS. 2 and 3A-3C. In the illustration of FIG. 3H, only the PR outer walls 134 are illustrated, but in the same etching operation 353, the PR channel walls 132 are formed.

Optionally, next, at 354, a washing operation occurs, followed by the attachment at 344 of applying 356 a hydroxysuccinimide (NHS) surface based on the zero background PEG (NHS-PEG) coating to the functionalization layer 341 in the sample sites within the sample site pattern. The NHS-PEG-X 356 will only attach to the SiN layer 341 in the hole 347 and not to the HMDS 345. At 357, another washing operation 357 occurs, followed at 358 by the attachment of samples 359 in the holes 347. After another washing operation at 360, the lid 361 is attached at 362.

In accordance with the foregoing process, flow cell and outer walls 132 and 134 are able to be formed directly on the silicon wafer 340 with a lid 361 formed directly onto the flow cell and outer walls 132 and 134. Hence, the first photo resist 346 is used to form the sample site pattern of holes to expose the SiN layer 341, while the second photoresist 352 is used to pattern the flow cell channels in any desired pattern, and DNA samples are bonded directly to the SiN layer 341 (functionalization layer).

The samples 167 are centered above pixel elements 170 during a current sample set inspection frame which includes a series of ASP. Before the ASP, the samples 167 are excited. Next, the set of samples 167 emit flourophores that are detected by the pixel elements 170. This process is repeated during each chemistry cycle through the sequence process.

In one exemplary embodiment, the flow cell channel 122 is loaded with labeled DNA strands which preferentially attach to the surface. In this embodiment amplification of the DNA strands is not necessary. For each chemistry cycle, the light source 107 (FIG. 1) emits a series of light pulses. With each light pulse, an electrical signal is transmitted by the light controller 115 of the light source 107 to the read out controller 151. Alternately, an external controller instructs the laser driver to emit a pulse and send a correlated electrical signal to the read out controller. Following each light pulse, some of the fluorophores will emit fluorescent photons, which may be detected by a pixel element 170. The alignment and sizing of the pixel elements, waveguide and samples is controlled such that there is a low probability that a photon from a fluorophore in one emitting sample will be absorbed by a pixel element that is adjacent and is not located directly under the emitting sample. When a photon is detected by a pixel element, a time measurement circuit inside the pixel is triggered. The time measurement circuit is stopped by a global signal from the readout controller 151. Alternately, a global signal starts the time measurement circuit, the photon arrival event stops it, or, if no photon arrives, the measurement is not recorded. The readout controller 151 provides the global signal to all of the pixel elements. The pixels are read at regular intervals (e.g., after each frame) either simultaneously (e.g., similar to a global shutter type operation), or row-by-row (e.g., similar to a rolling shutter type operation), or in blocks. Each time a pixel is read, both its photon count (# of collected events) and the cumulative time information are read out. Alternatively, the read out operation may be performed in response to a signal from the light source controller that a sufficiently large number of light pulses have been transmitted onto the samples. Then, the, aggregate time measurement information and photon count collected from each pixel element is read out as above and used to determine which one of the possible fluorophores is bound to the sample. The readout controller 151 may include a lifetime decay (LD) module 153 and a classification circuit 154 to identify a series of photons incident on the corresponding pixel element, to correspond to one of a set of predetermined label signatures. The LD module 153 is coupled to the DFP device 130. The LD module 153 is configured to receive, from each of the pixel elements, the time information and the photon count and based thereon to determine, for each of the pixel elements, a lifetime decay characteristic associated the sample located proximate to the corresponding pixel element. The classification circuit 154 stores a set of predetermined label signatures 156. The classification circuit 154 compares the lifetime decay characteristic, associated with the corresponding pixel element, to a set of predetermined label signatures 156 to identify a probe bound to the sample proximate to the corresponding pixel element. In an embodiment, the lifetime decay characteristic represents a mean arrival time (MAT) that is uniquely associated with one type of probe bound to the sample. In this example, the classification circuit 154 is configured to receive a separate MAT associated with each of the pixel elements and to identify a fluorophore having the photon emission signature corresponding to each MAT. Adjacent pixel elements may detect different MATs as the adjacent pixel elements may have samples bound to different probes. For example, pixel element #1 may have a MAT that corresponds to Fluorophore #1, while pixel elements #2-#10 have a similar MAT that corresponds to a different fluorophore #3.

Figure 4A:
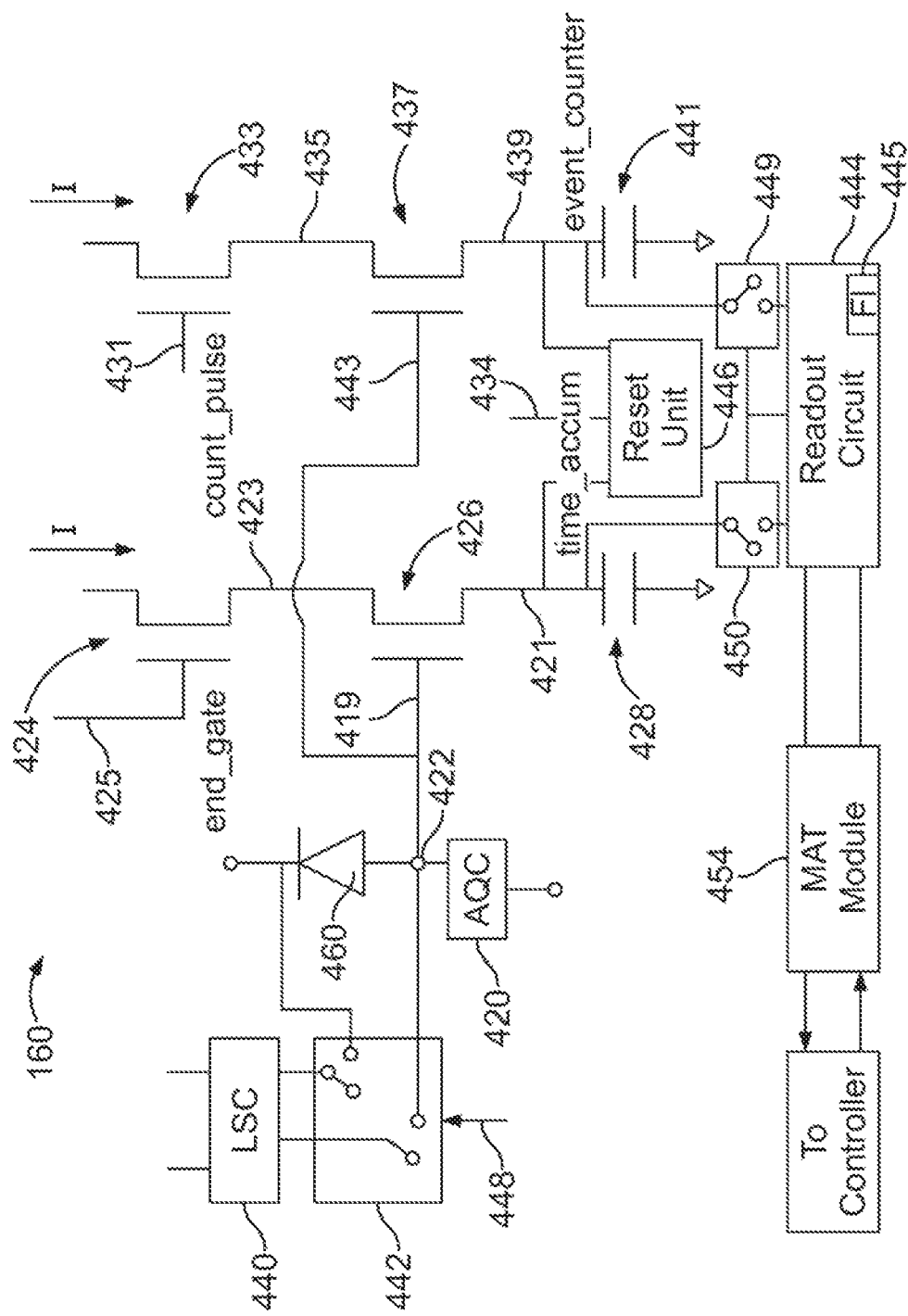
FIG. 4A illustrates a block diagram of a detection circuit that is provided within each pixel element in accordance with an embodiment.

FIG. 4A illustrates a block diagram of an in-pixel detection circuit or tixel 160 that is provided within each pixel element in accordance with an embodiment. As explained herein, the in-pixel detection circuit 160 tracks information and that enable calculation of the lifetime decay characteristic, such as a mean arrival time (MAT) for photons over a sampling period, generally referred to as a frame. The mean arrival time is derived from information that is collected by the in-pixel detection circuit. For example, the information may include a total number of photons detected by the pixel element and an accrued time interval from each event to the end of the associated detection window or ASP. Each in-pixel detection circuit includes a sensing device, such as a CMOS Single-Photon Avalanche Diode (SPAD). Each SPAD is a reverse-biased diode that operates beyond the breakdown point in order to measure photon time of arrival. The SPAD devices do not suffer from "read noise". In accordance with embodiments herein, the in-pixel detection circuits seek to reduce dark noise, increase pixel packing density, increase spectral response, and reduce cost. Each in-pixel detection circuit collects information sufficient to classify the fluorescence signal. Each in-pixel detection circuit outputs two analog voltages derived from many (10's to 100's) of photon arrival measurements. The in-pixel detection circuit reduces the data analysis necessary to analyze a large number of photon arrival measurements.

The information readout from the in-pixel detection circuits is then used to discriminate which sample (e.g., base) is present at a particular activation site based upon the fluorescence lifetime signature exhibited by the sample. An excited fluorescence electron will relax to a ground state after being excited for a certain "responsiveness" time. The responsiveness time is unknown, and stochastic. More specifically, the responsiveness time for an individual fluorescence electron is random. When a probability is plotted over time to illustrate the probability that an individual fluorescence electron will emit a photon, the probability distribution over time (responsiveness time probability) exhibits an exponentially decaying probability. The rate of decay of the responsiveness time probability is uniquely characteristic for each species of probe (e.g., each flourosphere) and the environment: P(t)=P0 exp (−t/t). When a collection of one type of probe (fluorophore) is excited, the responsiveness time probability can be detected as an intensity decay over time.

The rate of decay of the responsiveness time probability can be measured as a probe (fluorophore) lifetime decay characteristic or signature. A mean of an exponentially decaying probability is 1/rate of decay which equals tau (t) and represents one lifetime decay characteristic. Embodiments described herein include an in-pixel detection circuit that calculates the mean arrival time for multiple photons (events) that are sensed at tixel of interest over multiple ASP. A single data point, associated with the mean arrival time, is sufficient to determine a probe (e.g., fluorophore) lifetime signature.

A mean arrival time (MAT) module 454 may be provided on the same chip as the in-pixel detection circuitry, or on a common circuit board with the in-pixel detection circuitry or as part of a separate system controller. The MAT module 454 determines the MAT based on a sum of arrival times for a number of events/photons and based on the number of events/photons for which the arrival times are summed.

Each in-pixel detection circuit includes a temporal accumulator 428 and an event counter 441. The temporal accumulator 428 sums arrival times for a number of events/photons and the event counter 441 counts the number of events/photons, both for a predetermined period of time, also referred to herein as a frame. At the end of each frame, the readout circuitry 444 reads out two outputs, namely the value in the temporal accumulator 428 and the value in the event counter 441. The readout circuitry 444 then calculates a ratio, such as in accordance with the equations below, between the values from the temporal accumulator 428 and the event counter 441. As an example, the values may be voltage levels representative of an arrival time sum and of the number of events/photons. The ratio of the voltages is linearly related to the average time of arrival.

$$\frac{\Delta V_{accumulator}}{\Delta V_{counter}} = \sum_i \left( \frac{I \times (t_{end\_gate} - t_{arrival\_time(i)})}{C} \right) \bigg/ \left( \frac{n \times I \times t_{fixed\_width}}{C} \right) =$$

$$\frac{\sum arrival\_times}{\#events} =$$

$$\frac{n \times t_{end\_gate} - \sum_i t_{arrival\_time(i)}}{n \times t_{fixed\_width}} = const\_1 - \frac{\sum_i t_{arrival\_time(i)}}{n \times const\_2}$$

The tixel 160 includes a period activation switch 424 that defines active sensing periods in response to a global ASP timing signal 425 from the readout controller 151 (FIG. 1). Each of the active sensing periods has a start time and an end time. The period activation switch 424 changes state at the start and/or end times for each of the active sensing periods when the global timing signal 425 changes state. A group of active sensing periods are included in each frame.

The tixel 160 further includes a photon TOA detector element 460. The photon TOA detector element 460 is able to detect incidence of individual photons (e.g., within the wavelength range of 400 nm to 1100 nm) with relatively accurate precision (e.g., 0.1 nsec). For example, the photon TOA detector element 460 may represent an avalanche diode, single photon avalanche diode (SPAD), a silicon photomultiplier and the like. The element 460 senses each individual photon incident upon the element 460 and produces a photon incident signal on node 422 at the time that the photon impacts the element 460. A photon detector switch 426 changes state (e.g., closes) in response to the photon incident signal at node 422. In the example of FIG. 4A, the element 460 is illustrated with the cathode connected to a high positive DC voltage supply and the anode connected to node 422 that is electrically common with the gate inputs 419 and 443 of the photon detector switch 426 and photon count switch 437. The high positive voltage is slightly higher than the breakdown of the element 460. When the element 460 is disarmed, the anode is connected to the high voltage (up to VDD) such that the voltage across the element 460 is V_high-VDD<V_breakdown. When the element 460 is armed, the anode drops to a lower voltage, e.g., ground, such that the voltage on the element 460 is V_high>V_breakdown. In accordance with the above, the node 422 (and thus the gate inputs 419 and 443) is maintained between ground and VDD in order to avoid causing reliability issues with the switching transistor, namely the switches 426 and 437.

Optionally, the element 460 may be reversed, such that anode is connected to a power supply and the cathode is connected to node 422 that is electrically common with the gate inputs 419 and 443. When the cathode (the top node in FIG. 4A, which is the NWell node) is coupled to the gate inputs 419 and 443, then the anode is connected to a high negative DC voltage slightly lower than the breakdown voltage of the diode. When the element 460 is disarmed, the cathode is at ground and when the element 460 is armed, the element 460 is at a high voltage (up to VDD which is typically 3.3V).

In one embodiment, the switches 424 and 426 define start and stop times for an individual photon TOA count within a current ASP. The switch 426 starts the photon TOA count at the time that a photon is incident on element 460, while the switch 424 ends the photon TOA count. Alternatively, the switch 424 may start the photon TOA count and the switch 426 may end the photon TOA count. The start signal may come from the laser trigger and the end may come from the TOA pixel. The converse may also happen ("reverse start-stop").

The temporal accumulator 428 receives an input 421 from series switches 424 and 426, and tracks time information associated with photons incident upon the element 460 based on the input 421 and on the signal from node 422. The time information for an individual photon represents the time interval between an arrival of the photon (event occurrence time) and a beginning or ending of the detection window (ASP start or stop time). The temporal accumulator 428 maintains a running sum of the total TOA count time for multiple ASPs. The temporal accumulator 428 stores "cumulative time-related" information based on a multitude of photon arrivals at a single corresponding pixel.

An event counter 441 receives an input 439 from series switches 437 and 433, and tracks the number of photons/events that are sensed by the element 460. The event counter switch 437 has an input 435 that is serially connected to an output of an event counter switch 433 which receives an input signal 431 from a controller such as the readout controller 151. A power current I is supplied to inputs of the switches 424 and 433, which are opened and closed based on signals at the gate inputs 425 and 431. The event counter switch 437 and the photon detector switch 426 are turned on and off based on the signal from node 422 that is supplied the gate inputs 443 and 419.

The cumulative time-related and photon count-related information are accumulated during a series of the active sensing periods associated with a frame. For example, the time information may include at least one of a temporal center of mass, time-gate count ratios and time-gated photon flux associated with multiple photon TOA counts sensed over an equal or greater number of corresponding active sensing periods. The count-related information represents the number of events sensed by the element 460.

The element 460 will not receive a photon during every ASP. For example, the element 460 may only receive one photon out of every 1000 ASPs. In this example, the temporal accumulator 428 would track 500 photon TOA counts which occurs over 50,000 ASPs and the counter 441 would count 500 photons. The photon incident interval may represent a length of time between when an individual photon is sensed by the element 460 and the end time of the corresponding active sensing period during which the individual photon is incident upon the TOA element 460. Alternatively, the photon TOA count may represent a length of time between the start time of the corresponding active sensing period and when the photon is sensed by the TOA element 460. The time information accumulated represents a sum of a plurality photon TOA counts for the number of photons sensed by the element 460.

The readout circuit 444 is provided to communicate with the readout controller 151 to control read out of the time information and photon count from the array of tixels 160. The readout circuit 444 may include a classification circuit to identify a series of photons, incident on the corresponding pixel element, to correspond to one of a set of predetermined label signatures based on the time information and photon count.

The readout circuitry 444 controls the activation and readout of the pixels. The readout circuitry 444 may utilize a "rolling shutter" type readout pattern, in which the readout circuitry 444 serially steps through sets or groups of in-pixel detection circuits. For example, the in-pixel detection circuits within a first set are read out at one point in time and then reset. Next, the in-pixel detection circuits within a second set are read out at a second point in time and then reset. The readout circuit 444 steps or "rolls" through sets of in-pixel detection circuits.

Each of the tixels 160 includes a quenching component 420 connected to the element 460. The quenching component 420 (active or passive) causing a voltage drop to occur across the element 460 once an avalanche event begins to build up across the element 460 in response to incidence of a photon upon the element 460. The quenching component 420 is connected in series with the element 460 and defines the element output node 422 between the quenching component 420 and the element 460. The temporal accumulator 428 is coupled (indirectly) to the element output node 422. The temporal accumulator 428 accrues time information associated with multiple incident photons based at least in part on a voltage at the output node 422.

Pixel readout circuit 444 event counter switch 437: when the number of sensed photons reaches a predetermined programmed count limit, the pixel readout circuit 444 sets a "data ready" flag 445 to stop the temporal accumulation and to inform the readout controller 151 that the time information in the tixel 160 is ready to be read out. The programmed count limit is set to correspond to a number of photons that, at most, when detected, are sufficient to identify the signature of an individual label. The event counter switch 437 of the pixel readout circuit 444 controls reset of the temporal accumulator 428. For example, when the event counter 441 reaches the event count limit (e.g., 1000, 10,000, etc.), the pixel readout circuit 444 informs the readout controller 151 of this information. The readout controller 151 then sends a reset signal 434 to a reset unit 446. The reset unit 446 resets the event counter 441 and the temporal accumulator 428 to zero. Optionally, the readout circuit 444 may automatically reset the event counter 441 and temporal accumulator 428 once the time information is read from the temporal accumulator 428. In the foregoing manner, the event counter 441 and temporal accumulator 428 maintain synchronized operation with one another, are dumped (read) concurrently and are reset concurrently. Thus this circuit also serves as a saturation protection circuit for high photon fluxes.

Figure 4B:
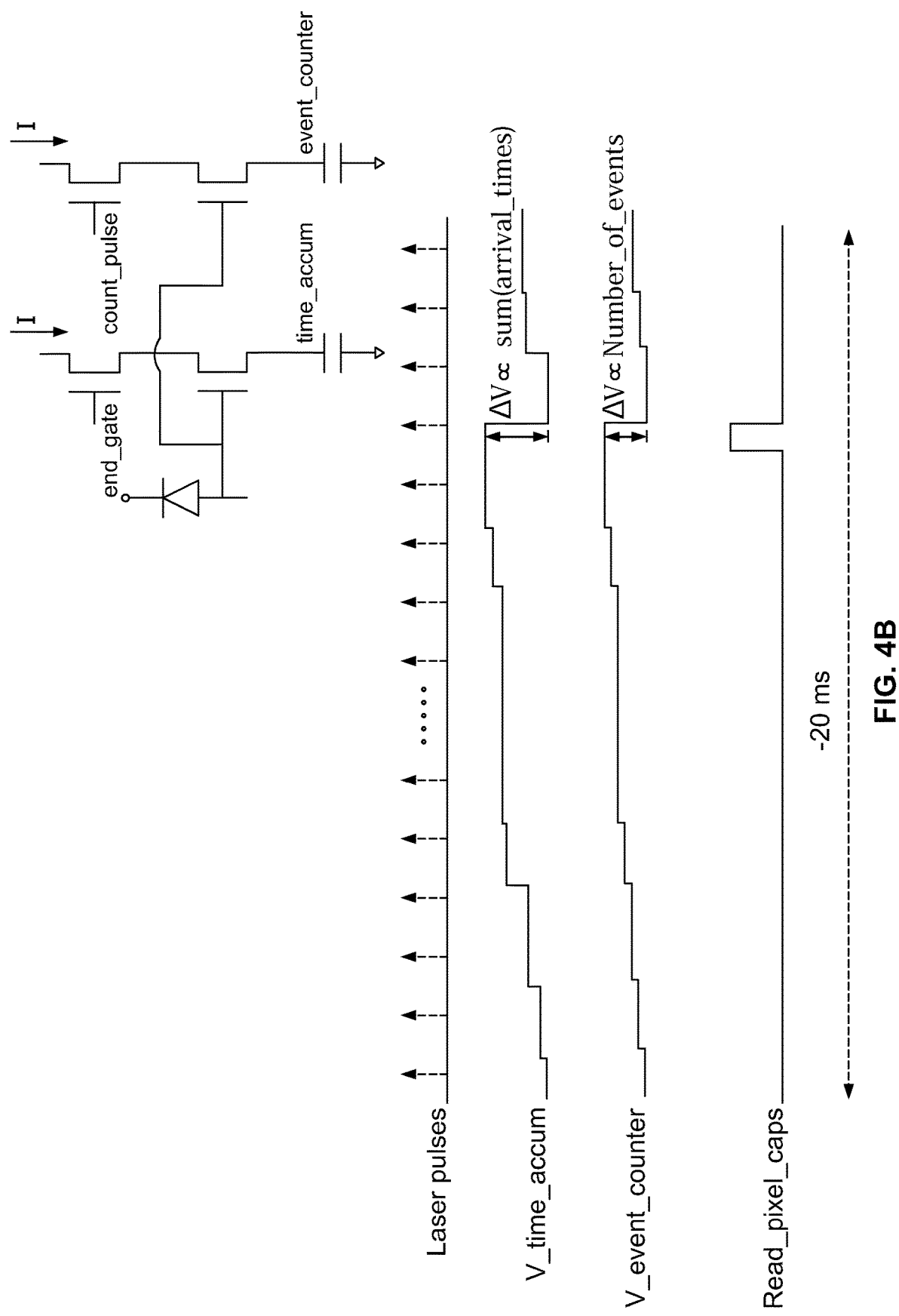
FIG. 4B illustrates a timing diagram for control signals utilized by an in-pixel detection circuit in accordance with an embodiment.

FIG. 4B illustrates a timing diagram for control signals utilized by an in-pixel detection circuit in accordance with an embodiment. The timing diagram includes the following signals i) a V_SPAD signal corresponding to an output signal from the element 460 at node 422, ii) an end_gate signal representing the control signal supplied at the gate input 425, iii) a V_time_accum charge representing the accumulated time-related charge stored on the temporal accumulator 428 during detection of a single photon, iv) a count_pulse signal representing the control signal supplied at the gate input 431 of the event counter 441 v) and a V_event_counter charge representing the event counter charge stored on the event counter 441 when a single photon is counted.

The timing diagram of FIG. 4B illustrates a time interval associated with a single ASP (e.g., during a 50 nsec interval). During the ASP operation, the V_SPAD is switched from a low state to a high state when a photon is detected. When the photon is detected, the temporal accumulator 428 begins increasing a level of the charge thereon. The temporal accumulator 428 increases the level of charge stored thereon until the end_gate signal 425 changes from a high state to a low state in order to close switch 425. When the switch 425 is closed, the temporal accumulator 428 stops increasing charge associated with the current photon. In the example of FIG. 4B, an arrival time interval of approximately 20 nsec. may occur between the photon arrival time and the high-to-low state change in the end_gate signal. When the arrival time interval is shorter, the amount of charge added to the temporal accumulator 428 is less. When the arrival time interval is longer, the amount of charge added to the temporal accumulator 428 is greater.

As noted above, during the ASP interval, the V_SPAD signal changes to a high state when the photon is detected. The V_SPAD signal, which is connected from node 422 to the gate input 443, closes the switch 437. However, initially, the switch 433 is open while the count_pulse signal is low. The count_pulse signal switches to a high state periodically, once during each ASP and for a short fixed interval width. The count_pulse signal, applied to the input gate 431, closes switch 433. The count_pulse signal returns to the low state after the fixed interval width and opens the switch 433. When the count_pulse signal and the V_SPAD signal are both high, then switches 433 and 437 are closed, thereby delivering current I from a source to the event counter 441 for the duration of the fixed interval window. The event counter 441 increases the charge thereon by an amount based on the duration of the fixed interval of the count_pulse.

In accordance with the foregoing process, the charge stored on the event counter 441 increases by a fixed amount (deltaV_count) each time a photon is detected. The charge stored on the temporal accumulator 428 increases by a variable amount (deltaV_accum) each time a photon is detected. The variable amount deltaV_accum is associated with the arrival time of the photon, where the arrival time corresponds to the length of time between photon arrival and the end of the ASP. Optionally, the arrival time corresponds to the length of time between photon arrival and the start of the ASP.

Figure 4C:
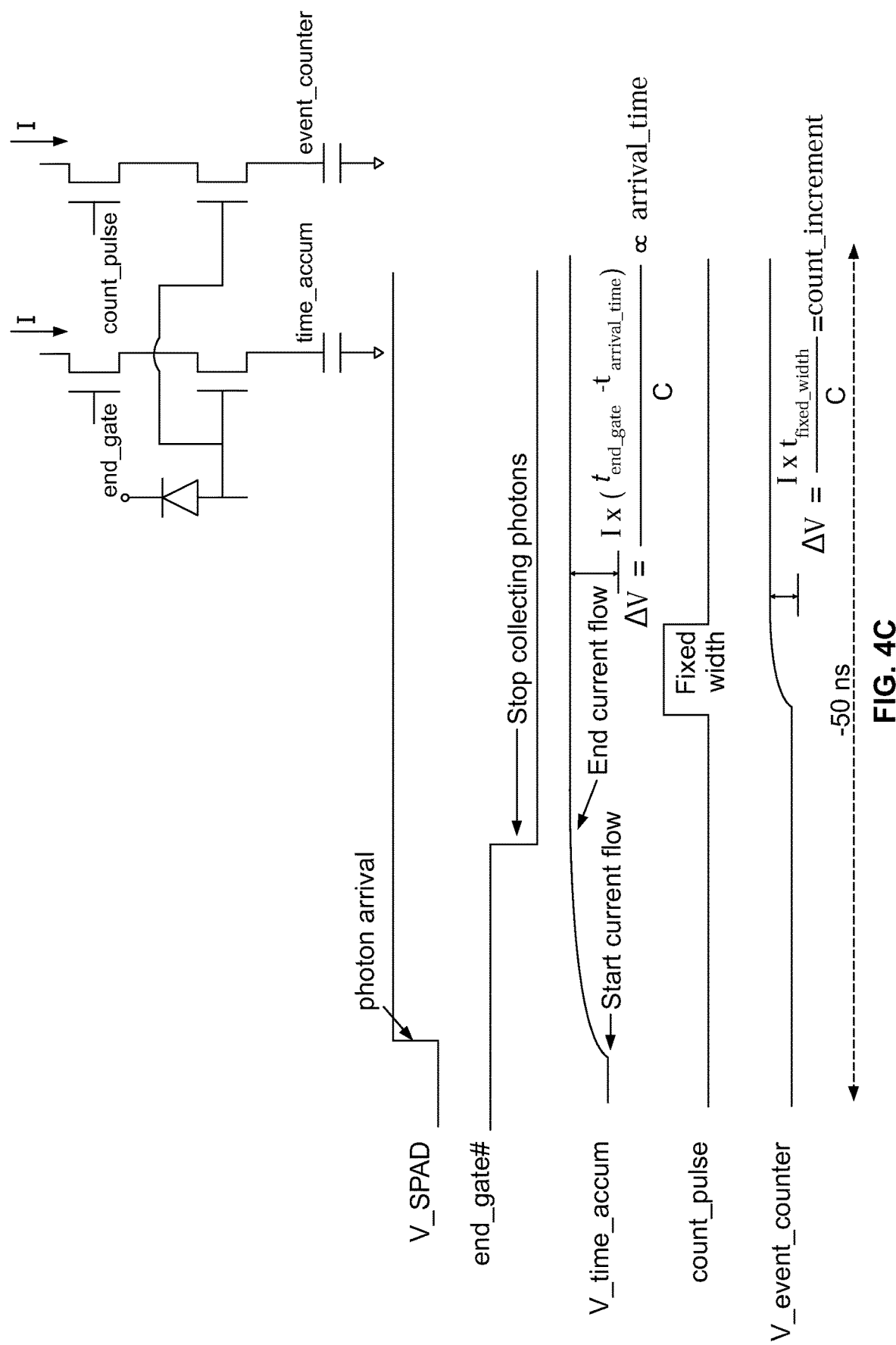
FIG. 4C illustrates a timing diagram associated with a photon detection frame.

FIG. 4C illustrates a timing diagram associated with a photon detection frame. Each photon detection frame includes multiple ASPs (e.g., a 20 msec interval that includes multiple 50 nsec. ASPs). During the frame, a series of laser pulses are transmitted, with one laser pulse per ASP. The arrival time charge (V_time_accum) stored by the accumulator 428 increases in a variable stepped manner during each ASP in which a photon is detected. An amount of each arrival time charge increase is dependent upon the length of the arrival time. Hence, as illustrated in FIG. 4C, the V_time_accum total increases in steps of different amounts during each ASP over the frame. The photon count charge (V_event_counter) stored by the event counter 441 increases in an event stepped manner during each ASP in which a photon is detected. An amount of each photon count charge increase is equal and corresponds the length of the fixed width of the count-pulse. Hence, the V_event_counter total increases in steps of equal event amounts during each ASP over the frame.

During each photon detection frame, the readout circuit 444 delivers a pulse as a read_pixel_caps signal to direct switches 449 and 450 to close in order to output the charge (time-related accumulation information and photon count information) stored in the accumulator 428 and the photon counter 441 to the readout circuit 444.

Figure 4D:
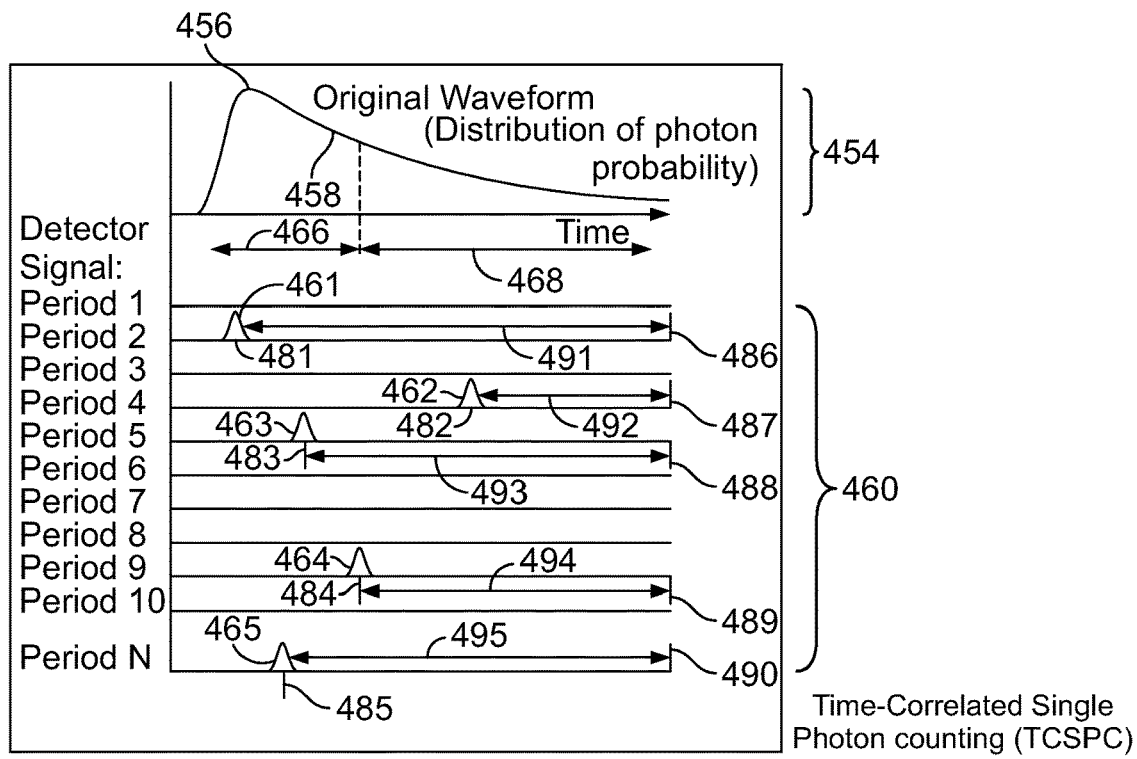
FIG. 4D illustrates a timing diagram in connection with an emission signature for a fluorophore detected in accordance with an embodiment.

FIG. 4D illustrates a timing diagram in connection with an emission signature for a flurosphore detected in connection with an embodiment of the present invention. In FIG. 4D, the horizontal axis corresponds to time while the vertical axis corresponds to energy amplitude. A top portion 454 illustrates a representative emission pattern for an individual fluorescence label. As shown in the pattern 454, after excitation, the fluorescence label exhibits a peak 456 in the emission probability, followed by a decreasing emission probability.

As explained hereafter, in accordance with various embodiments described herein, timing information is recorded and accumulated in connection with the detection of photons 461-465 over a large number of ASP periods. The time information does not represent a raw count of the number of photons sensed during any individual time bin. Instead, the time information represents a time interval between the time of arrival (481) of an individual photon (e.g., 461) and the beginning or end of the corresponding ASP. In the example of FIG. 4D, this time interval is denoted at 491 in connection with the photon 461 detected during period 2. The time interval 491 represents the time between the time of arrival 481 and the end 486 of the ASP period 2. Each of photons 462-465 similarly have a corresponding time interval 492-496 beginning at the time of arrival 482-485 and extending until the end 487-490 of the corresponding period 4, 5, 9 and n, respectively. The time intervals 491-495 are summed by the temporal accumulator to accrue a total time information, also referred to as the "total signature accrual time", that is uniquely associated with the signature of the fluorescence label being excited.

Returning to FIG. 4A, embodiments described herein utilize temporal filtering to separate excitation light from emission light. Detection by the DFP device 130 is managed by a controller (e.g., the system controller 111a, light controller 115 or read out controller 151) such that, during excitation by the light source 107 through the waveguides 118 of the samples 167, the tixels 160 are shut off or rendered not sensitive to light (also referred to as disarmed or discharged). Once the excitation light is stopped, the controller turns ON (arms or charges) the tixels 160 to become sensitive to emission photons from the samples 167. As explained herein, the tixels 160 may utilize SPAD type detectors. The diode within a SPAD detector is not triggered by photons while the voltage potential across the diode is below the diode breakdown voltage. Once the voltage potential across the diode is charged to above the diode breakdown voltage then the SPAD becomes sensitive to photons. Hence, during excitation by the light source, the tixels 160 become insensitive to photons by reducing the potential across the diodes to below the breakdown voltage. Following excitation, each tixel 160 is caused to become sensitive to photons by charging or raising the potential across the diode to above the breakdown voltage.

A certain amount of time is needed to raise the voltage potential across each diode to above the breakdown voltage. As an example, it may take 1-2 nsec to raise the voltage potential to above the breakdown voltage. The DFP device 130 includes a large number of tixels 160 (e.g., millions). The sensitivity and accuracy of the tixels depends on the voltage across the diodes and, thus to ensure response uniformity the supply voltages must be kept uniform and constant despite the large instantaneous currents drawn by individual diodes as they break down. This requires a large supply of charge supplied quickly to discharged SPADS. Similarly, because all of the tixels, or a large number of the tixels need to be recharged simultaneously, large reservoirs of charge are required. By way of example, charge reservoirs are implemented as capacitors. When very large capacitances are needed, off-chip capacitors are used. However, off-chip charge must flow through metal wires on and off the chip and between the die and its package, thus encountering high inductance and resistance, which slow down the flow of charge. In order to obtain a desired quantum efficiency of the elements 460, the voltage swing across the elements 460 SPADs similarly should be maintained at a desired level, such as maximized. The V_off state occurs just below breakdown during which the elements 460 are off. The V_on occurs when V off+V_overbiads, with the V_overbias level being close to the digital supply voltage, during which the elements 460 are on. However, when a reservoir capacitor is used to supply charge to the elements 460, charge sharing occurs and the voltage on the elements 460 is approximately V_reservoir×C_reservoir/(C_reservoir×C_SPAD). Therefore, the required reservoir capacitance should be substantially larger that the element 460 reservoir (e.g., 10 times higher). A problem may arise in that 90% of the silicon area may be used for capacitance and not for detection. According to embodiment described herein, the guard ring around the elements 460 is utilized for this local charge storage by using structures raised above the substrate in order to store charge. These change storage structures simultaneously also protect sensitive regions of the device from undesirable illumination.

In accordance with an embodiment herein, the DFP device 130 is constructed such that each tixel 160 or small groups of tixels 160 are coupled locally to an individual local storage capacitor 440 that is provided in the substrate 150, or, preferentially, above the substrate, either as a MiM capacitor (2 metal layers with a very thin dielectric between), or as a MoM capacitor (a stack of metal plates such that Mx and Mx+1 are separated by a dielectric but Mx+1 and Mx+2 are electrically connected. These metal layers provide a charge reservoir that is integrated with the pixel element. For example, if the DFP device 130 includes 10,000 tixels 160, then 10,000 local storage capacitors 440 may be provided, with each local storage capacitor 440 provided within the corresponding tixel 160. Optionally, each local storage capacitor 440 may be coupled to a group of tixels 160 (e.g., 10-100). The local storage capacitors 440 induce a desired voltage potential across corresponding ones or groups of the TOA elements 460. For example, the local storage capacitors 440 may be formed in the same layer of the substrate 150 as the SPADs, or alternatively formed in an adjacent layer above the substrate 150.

In FIG. 4A, a local storage capacitor 440 has output terminals that are connected through a charge switch 442 across the TOA element 460. When the output terminals of the storage capacitor 440 are connected to the TOA element 460, the storage capacitor 440 applies a voltage potential across the storage capacitor 440 that is above the breakdown voltage of the element 460. The storage capacitor 440 has input charge terminals that receive supply charge from an external source, in order to maintain a charge across the storage capacitor 440 at all times that is sufficient to raise the potential across the element 460 to above the breakdown voltage.

The switch 442 is controlled by a recharge signal 448 delivered from the read out controller 151. The recharge signal 448 causes the switch 442 to close before the global ASP timing signal 425 directs the period activation switch 424 to close, thereby ensuring that the storage capacitor 440 applies a voltage potential across the storage capacitor 440 that is above the breakdown voltage of the element 460 before or at the beginning of the ASP.

Figure 4E:
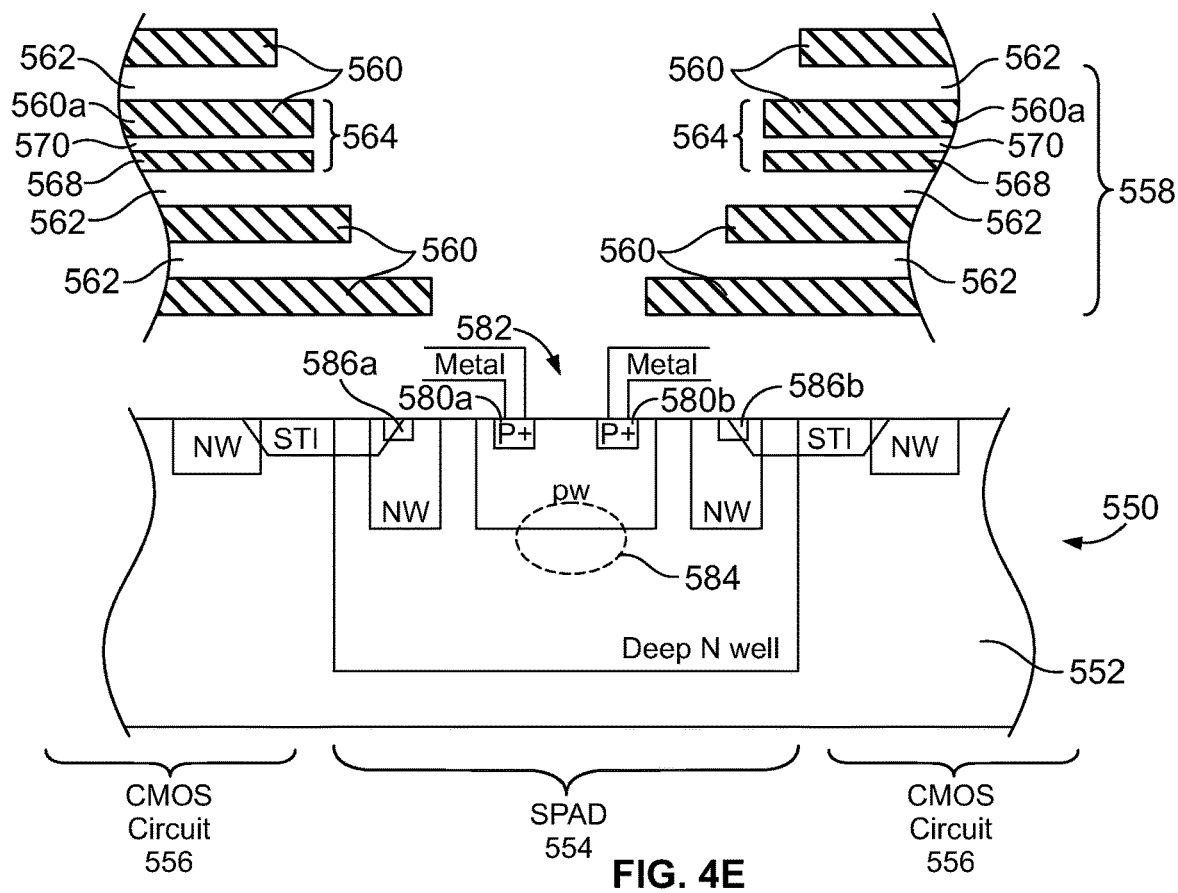
FIG. 4E illustrates a cross-sectional model to illustrate one manner for integrating the local charge storage capacitor with a pixel element.

FIG. 4E illustrates a cross-sectional model to illustrate one manner for integrating the local charge storage capacitor with a pixel element. In FIG. 4E, a portion of a of a DFP device 550 that includes a substrate 552, in which a pixel element 554 and CMOS circuitry 556 are formed. A mask layer 558 has embedded therein a collection of metal layers 560 that are stacked upon one another, but spaced apart from one another by gaps 562 filled with an inter-metal dielectric (e.g. silicon dioxide). The metal layers 560 collectively block light from impinging upon the electronics in the DFP device.

The pixel element 554 includes terminals 580a and 580b, and terminals 586a and 586b, that are joined to external metal conductors. The terminals 580a and 580b have an exposure active region 582 there between in which photons are incident. The pixel element 554 defines a diode in the depletion region (generally denoted at 584) formed between the P well and the deep N well.

A local storage capacitor 564 is formed within the mask layer 558. The local storage capacitor 564 is formed from a metal capacitor bottom plate 568 located adjacent and spaced apart from metal layer 560a. The bottom plate 568 is separated from the metal layer 560a by a thin dielectric layer 570. The metal layer 560a is connected to a DC power supply. The bottom plate 568 of the local storage capacitor 564 is electrically connected to one of the terminal 580a, 580*b*, 586*a* and 586*b* of the pixel element 554 through a switch, such as switch 442 (FIG. 4A). The local storage capacitor 564 charges up to a predetermined charge level while disconnected from the pixel element 554. When it is desirable to connect the local storage capacitor 564 to the pixel element the bottom plate 568 is connected to a desired terminal of the pixel element 554, to transfer/share the stored charge with, and introduce a voltage potential across the pixel element 554.

When a given packet of optical energy needs to illuminate an array of molecules using channel waveguides, the power reaching the site farthest from the source will be $P_0 \times A/n \times L(l)$ where $P_0$ is the source power, A is the cumulative attenuation due to imperfect coupling of the light from the source to the input of the channel waveguides, n is the number of channel waveguides and L(l) is the length-dependent attenuation of the propagating optical signal. Thus, to maximize the power delivery efficiency, it is desirable to limit the propagation distance of the channel waveguides, for a given number of channels. This is achieved using new topologies where the pixel distribution is asymmetric, namely the pixel distribution is short in the direction of the waveguides and, to compensate, loner in the orthogonal direction (so the total pixel area is maintained).

Figure 5A:
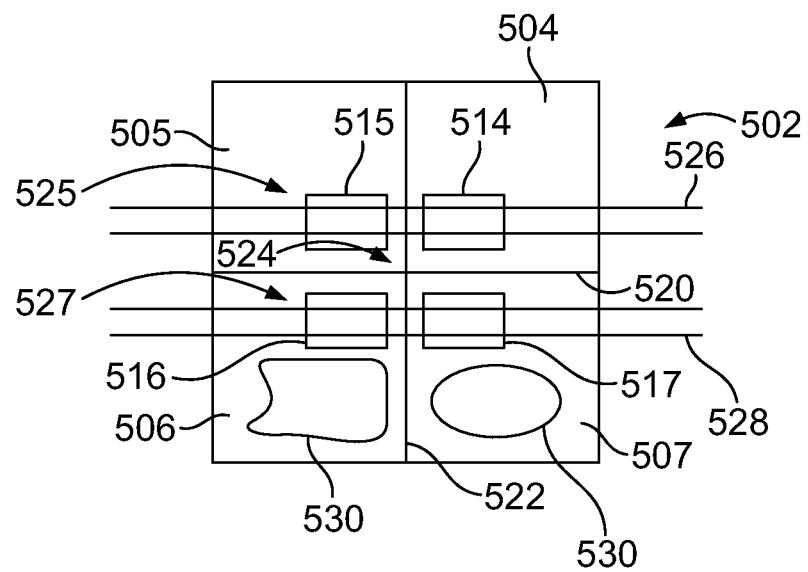
FIG. 5A illustrates a cluster of TOA elements in accordance with an embodiment.

FIG. 5A illustrates a cluster 502 of TOA elements 504-507 with an asymmetric pixel distribution. Each TOA element 504-507 is associated with a single SPAD detector and includes a corresponding active area 514-517. The active areas 514-517 are not centered within a "footprint" of the corresponding TOA elements. Instead, the active areas 514-517 are offset (or clustered) to be located proximate one corner of the corresponding TOA elements 504-507. The TOA elements 504-507 have perimeters that abutted against one another along interfaces 520 and 522. The TOA elements 504-507 are then oriented relative to one another such that the active areas 514-517 are located immediately adjacent one another and adjacent a center 524 of the cluster 502. The active areas 514 and 515 are grouped in a set 525, while the active areas 516 and 517 are grouped in a set 527. Sets 525 and 527 are aligned with fluid flow paths of channels 526 and 528.

The arrangement illustrated in FIG. 5A groups the active areas 514-517 to form a denser collection active area in a region within the cluster 502. As one example, the active areas 514-517 may be grouped to form rows that reside along and directly below a fluid flow path 526 and 528. As explained above, samples will generally be positioned within the flow cell channel generally along a center line of the flow cell paths 526 and 528 that will similarly correspond to the centers of the. The active areas 514-517 within each set 525 and 527 of TOA elements 504-507 are grouped close to one another along the corresponding central lines.

The electronics within each TOA element 504-507 may be provided somewhat remote from the active areas 514-517. By way of example, the electronics may be provided within region 530 of each TOA element 504-507.

Figure 5B:
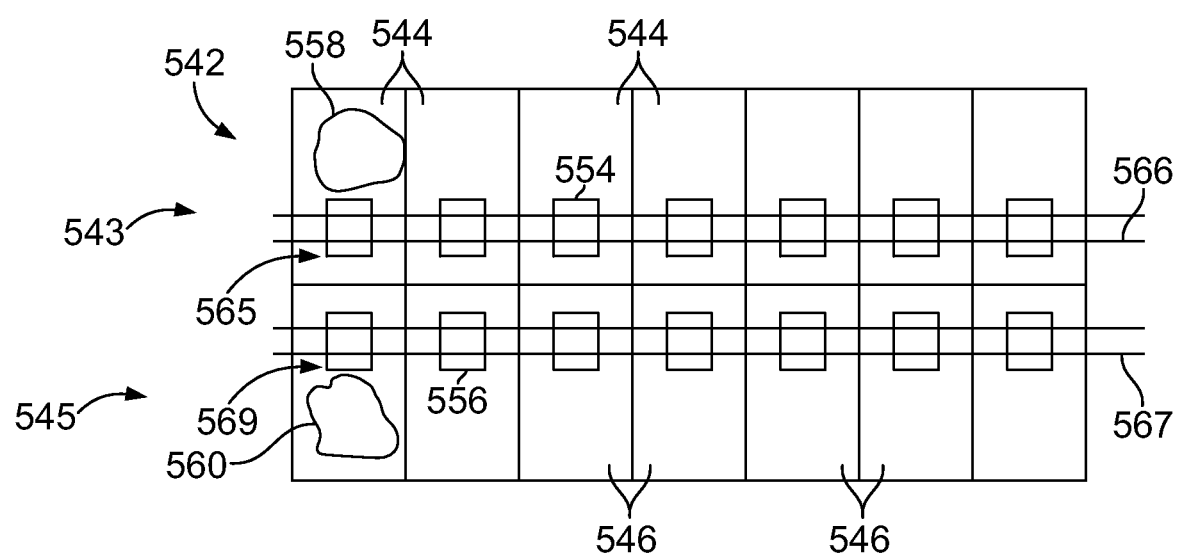
FIG. 5B illustrates an alternative configuration for a cluster in accordance with an embodiment.

FIG. 5B illustrates an alternative configuration for a cluster 542 which is arranged to enhance channel waveguide illumination. When a given packet of optical energy needs to Illuminate an array of molecules using channel waveguides, the power reaching the site farthest from the source will be $P_0 \times A/n \times L(l)$ where $P_0$ is the source power, A is the cumulative attenuation due to imperfect coupling of the light from the source to the input of the channel waveguides, n is the number of channel waveguides and L(l) is the length-dependent attenuation of the propagating optical signal. Thus, to maximize the power delivery efficiency, it is desirable to limit the propagation distance of the channel waveguides, for a given number of channels. This is achieved using new topologies where the pixel distribution is asymmetric, namely the pixel distribution is short in the direction of the waveguides and, to compensate, longer in the orthogonal direction (so the total pixel area is maintained).

The cluster 542 includes two sets or rows 543 and 545 of TOA elements 544 and 546, respectively. The elements 544 have active areas 554 grouped or arranged in one set 565. The elements 546 have active areas 556 also grouped or arranged in a second set 569. The active elements 554 in set 565 are aligned substantially with a fluid flow path 566 and waveguide within one fluid flow channel. The active elements 556, arranged in the set 569, are centered along a separate (adjacent) fluid flow path 567 and waveguide of an adjacent fluid flow channel. The active areas 554 and 556 are offset from the centers of the elements 544 and 546, respectively. The elements 544 and 546 have regions 558 and 560 in which the electronic components may be provided.

The configurations of FIGS. 5A and 5B enable active areas to be locally grouped with respect to the locations of samples and relative to fluid flow cells, while providing large areas upon each element to be dedicated to electronic components. The blocking layers or masking layers may be configured to entirely block off and isolate the regions 558, 560 and 530 to prevent excitation or emission light from impinging upon the electronics within the substrate.

Figure 5C:
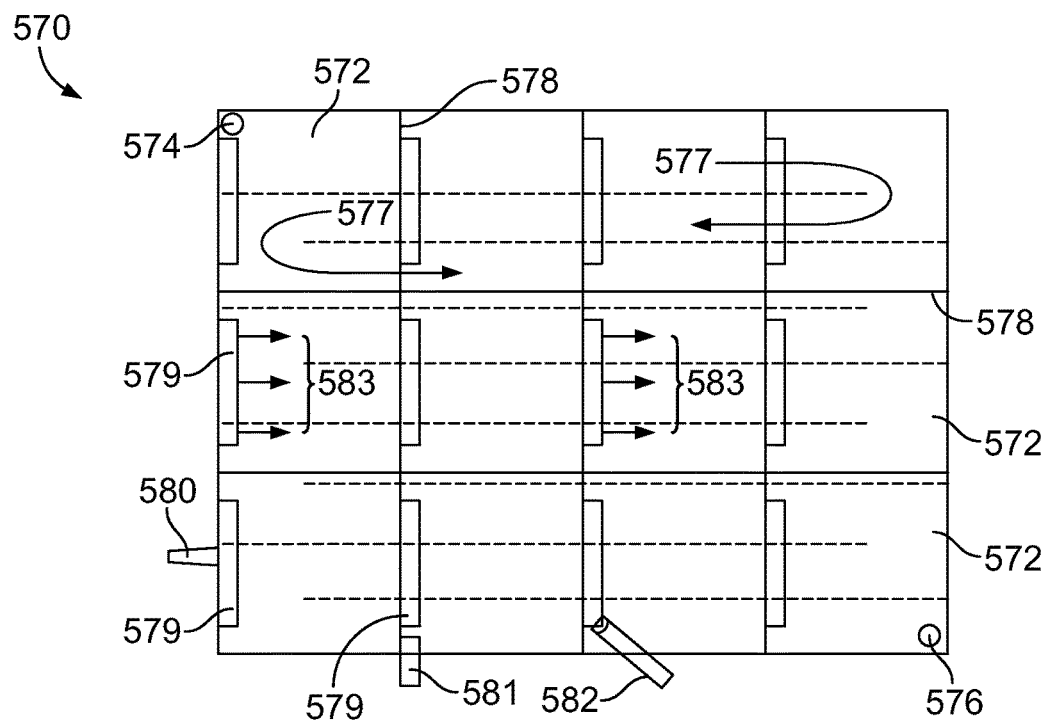
FIG. 5C illustrates a DFP device in accordance with an embodiment.

FIG. 5C illustrates a DFP device 570 having a fluid inlet 574 and a fluid outlet 576. The DFP device 570 is divided into multiple sub arrays 572 that are joined to or abutted against one another at interfaces 578 to form a grid. Each sub array 572 includes a corresponding grating 579 that receives light at an inlet, splits the light and produces multiple light outlets 583. The light outlets deliver light to corresponding waveguides. In the example of FIG. 5C, light introduces 580-582 are shown to be optically coupled to corresponding gratings 579. The introducers 580-582 may be oriented at various angles with respect to the grating. For example, the introducer 580 may be perpendicular to an end of the DFP device 570. The introducer 581 may be perpendicular to a side of the DFP device 570. The introducer 582 may be perpendicular to a bottom surface of the DFP device 570.

Flow cell walls are shown in dashed line to separate flow cell channels along a fluid flow path 577. As shown in FIG. 5C, the flow cell channels extend across multiple sub arrays 572.

Optionally, a single excitation light source may be provided as a common source for all sub arrays 572. Optionally, separate excitation light sources may be provided for each sub array 572, such that each grating 579 has a separate light source.

Figure 5D:
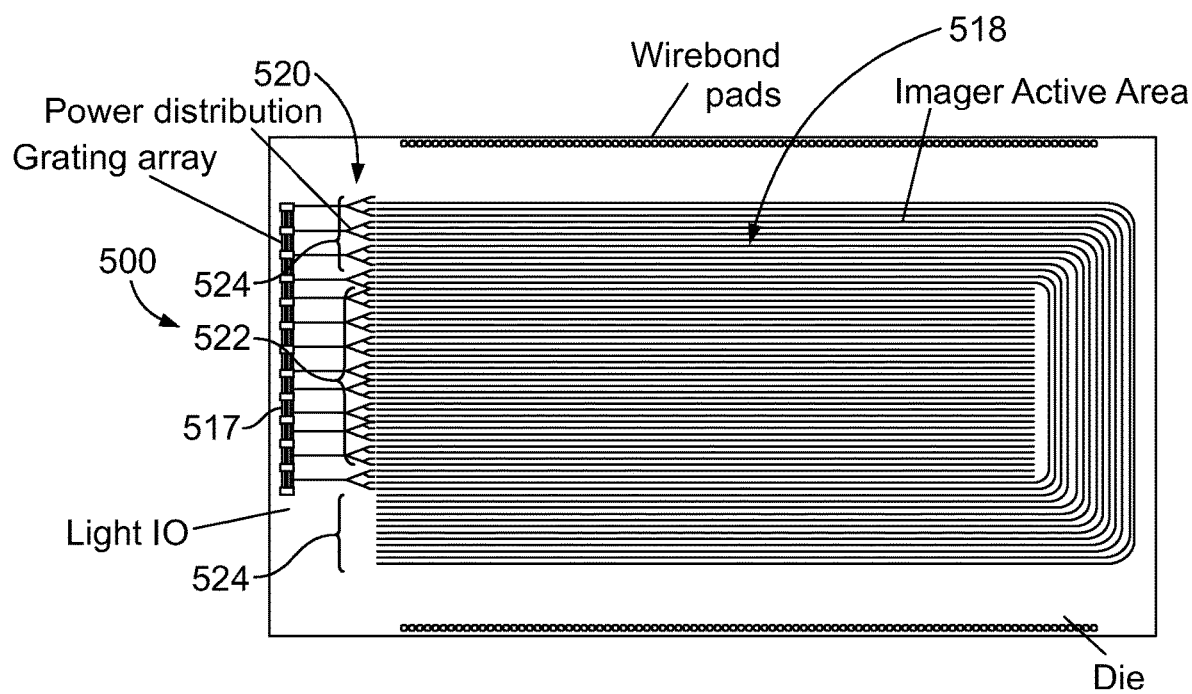
FIG. 5D illustrates a layout for the photonics layer of a DFP device formed in accordance with an embodiment.

FIG. 5D illustrates a layout for the photonics layer 500 of a DFP device formed in accordance with an embodiment. The photonics layer 500 includes a grating 517 at which light is introduced. Optical channels guide light from the grating 517 to a series of beam splitters 520. The beam splitters 520 separate the power of inlet beams into individual light beams that are directed onto each waveguide 518.

The waveguides 518 may have different shapes. For example, one set of waveguides 518 may represent an interior set 522, while another set represent a peripheral set 524. The waveguides 518 in the interior set 522 are linear, while the waveguides in the peripheral set 524 extend in a curved manner about the interior set 522.

Figure 5E:
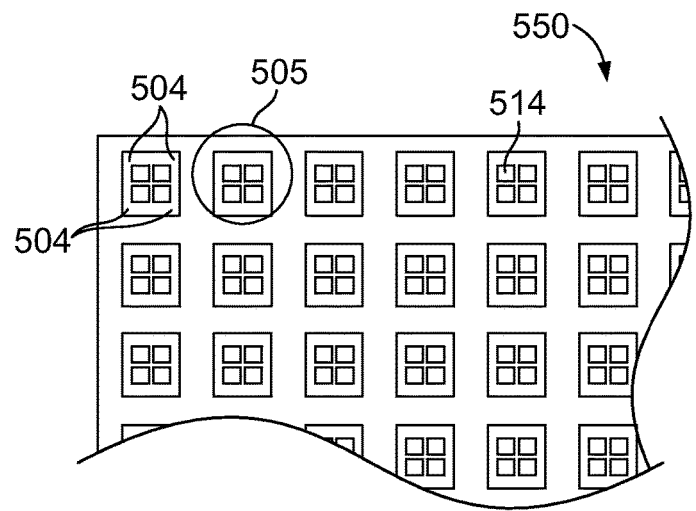
FIG. 5E illustrates a top view of a portion of a DFP device formed in accordance with an embodiment.

FIG. 5E illustrates a top view of a portion of a DFP device 550. The DFP device 550 includes an array of TOA elements 504, where quad groups (4) of TOA elements 504 form clusters 505. Each TOA element 504 has an active area 514 that is offset from a center of the TOA element 504. The active areas 514 are grouped in each cluster 505. The clusters 505 are arranged in rows and columns that are aligned with corresponding fluid flow paths.

Figure 5F:
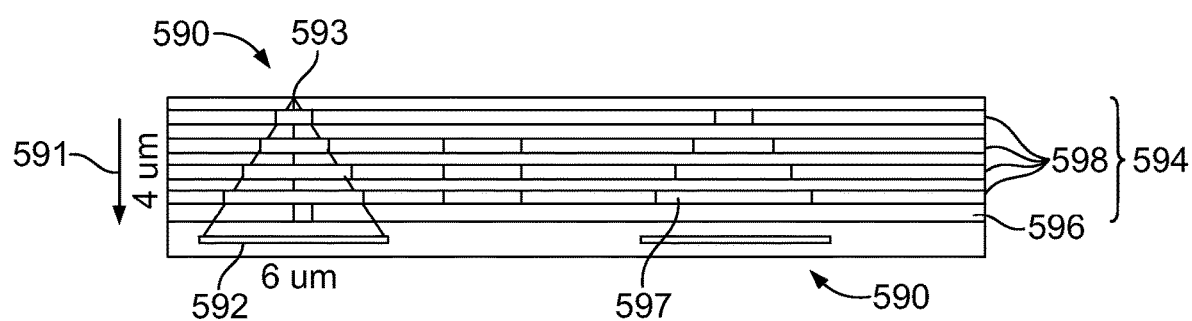
FIG. 5F illustrates a side sectional view through a pair of pixel elements formed in accordance with an embodiment.

FIG. 5F illustrates a side sectional view through a pair of pixel elements 590. The pixel elements 590 each include a SPAD active area 592 below a mask layer 594. The mask layer 594 includes an IMD substrate 596 with a series of blocking layers 598 spaced apart by gaps 599. The blocking layers 598 have mask apertures 597 there through that have widths that progressively become larger when moving along the depth 591 of the IMD substrate 596 away from the sample 593 toward the SPAD active area 592.

Figure 6:
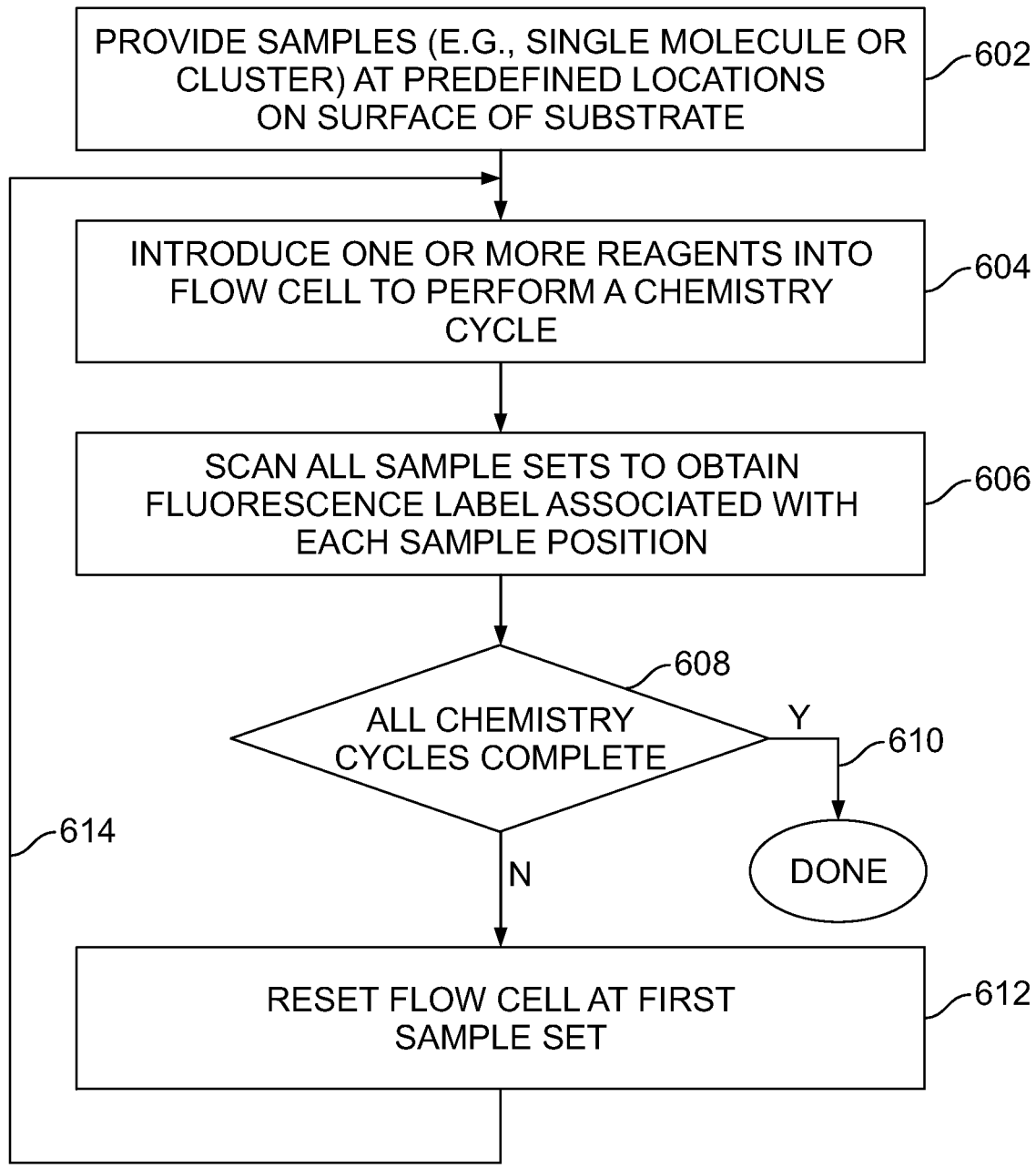
FIG. 6 illustrates a sequencing process carried out by the sequencing subsystem in accordance with an embodiment.

FIG. 6 illustrates a nucleic acid sequencing process carried out by the sequencing subsystem 110 in accordance with an embodiment. At 602, nucleic acid samples 167 are provided at individual locations or sites on the surface of the functionalization layer 144 along each flow cell channel 122. The nucleic acid sample can be single molecules that are optically distinguishable from each other under the detection techniques used or, alternatively, the nucleic acid samples can be clusters of nucleic acids that are detected as ensembles of several nucleic acid molecules at an addressable location. Optionally, the samples 167 at 602 may be provided randomly on the surface of the functionalization layer 144. At 604, one or more reagents are introduced into the DFP device 130. The reagents are introduced during a chemistry cycle in accordance with a fluidics protocol. Any of a variety of reagents can be added as appropriate for a particular sequencing technique. Exemplary reagents include, but are not limited to, nucleotides, nucleotide analogs such as those having labels and/or extension blocking moieties, polymerases, oligonucleotides, oligonucleotide analogs such as those having labels and/or extension blocking moieties, ligases, deblocking agents to remove blocking moieties, or wash solutions. Other useful reagents are set forth below in regard to various sequencing protocols as in the related references. In the example of FIG. 6, the chemistry cycle is synchronized with the detection session. Optionally, as explained below, the chemistry cycle and detection session may operate non-synchronous.

At 606, a detection step is performed for all of the samples 167 located on the functionalization layer 144 in order to collect time and photon count information. The detection step can be carried out for example, by scanning the surface of the substrate. The detection step may include multiple sample set inspection frames, each including a series of active sensing periods. At 608, a determination is made as to whether all chemistry cycles in accordance with a protocol have been completed. When all chemistry cycles are completed, flow moves along 610 and the process is done. Alternatively, when additional chemistry cycles remain to be completed, flow moves to 612. At 612, the DFP device 130 is reset, such as by clearing the temporal accumulator and photon counters and disarming the pixel elements. Flow then moves along 614 and the operations at 604 to 608 are repeated for the next chemistry cycle. The process is repeated until all chemistry cycles are complete.

Figure 7:
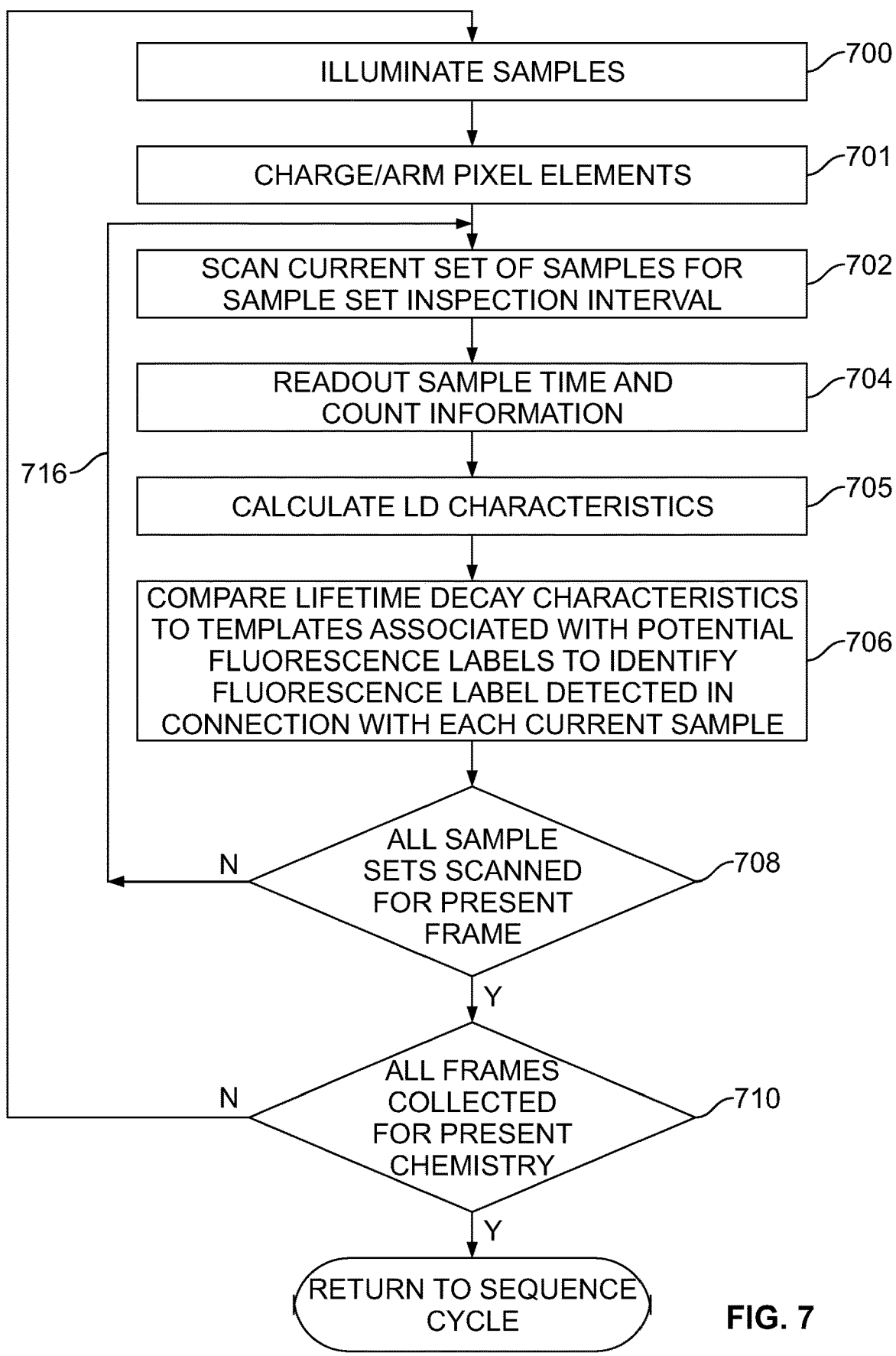
FIG. 7 illustrates a processing sequence carried out during the scanning operation of FIG. 6 in accordance with an embodiment.

FIG. 7 illustrates a processing sequence carried out during the detection operation at 606 (FIG. 6) in accordance with an embodiment. At 700, the sample sites are illuminated by a light source while the pixel elements are disarmed. At 701, after the light source is turned off, the pixel elements are armed such as by changing the SPADs to an active change level. At 702, a scan or other detection step is performed for the samples 167 on the functionalization layer 144. The scan or detection event at 702 lasts for the sample set inspection frame (which includes multiple ASP). Throughout the sample set inspection frame, photon TOA counts are accumulated over the multiple ASPs and the event count is incremented for each detected photon, at each pixel element. At 704, the time and count information recorded in the pixel elements 170 of the IC photon detection layer 155 for the current sample set inspection frame is read out to the readout controller 151. The readout controller 151 records the time and count information in connection with each sample position (pixel element for the current set of samples 167.

While the operation at 704 is shown to follow the operation at 702, optionally the operations at 702 and 704 may be interleaved and run in parallel. For example, the time information for individual pixel element(s) may be read out during the sample set inspection frame, but between ASP, when the corresponding data ready flag(s) 431 become set. For example, between each ASP or between groups of ASP, the read out controller 151 may sample some or each pixel readout circuit 444 to determine whether the corresponding data ready flag 445 is set. Once the data ready flag 445 is set for an individual tixel 160 thereafter, at any time during the sample set inspection frame, the time information is available for read out, before the end of the sample set inspection frame. For example, the readout controller 151 may check flags 431 for success groups of rows of pixel elements during or after sets of ASPs. The read out controller 151 may then readout time and count information for rows of pixel elements or for individual pixel elements.

At 705, the time and count information are used to calculate a lifetime decay characteristic (e.g., a MAT) for the probes at each sample site.

At 706, the LD characteristics used to derive for the current set of samples is compared at the readout controller 151 to a group of signature templates. Each signature template is associated with a unique potential label. For example, the signature templates may indicate a mean arrival time that should be associated within a pixel element when such pixel element receives emissions from a particular fluorescence label. For example, a fluorescence label having a wavelength of 570 nm, may exhibit a MAT value of between 0.05 ns and 0.50 ns. Alternatively, a different fluorescence label having a different wavelength which may generate MAT at a corresponding pixel element of between 0.1 ns and 1.0 ns. The comparison at 706 is performed in order to identify which fluorescence label was detected at each pixel element for the corresponding current sample position. At 706, the identified labels are recorded in connection with each associated individual sample position. It will be understood that labels can be distinguished by means other than comparison to a signature. For example, the time information can be classified to distinguish the label from which it was derived. In some embodiments, classification can be carried out by an analog to digital converter or 2 bit decoder.

At 708, it is determined whether all of the set of samples on the substrate have been detected or scanned. When all of the sample sets have been detected or scanned, flow moves to 710. Alternatively, when additional sample sets remain to be scanned at 702, flow returns to 702.

At 710, it is determined whether additional frames are to be collected for present chemistry. If so, flow returns to 700. If not, flow returns to point 508 in FIG. 6.

Figure 8:
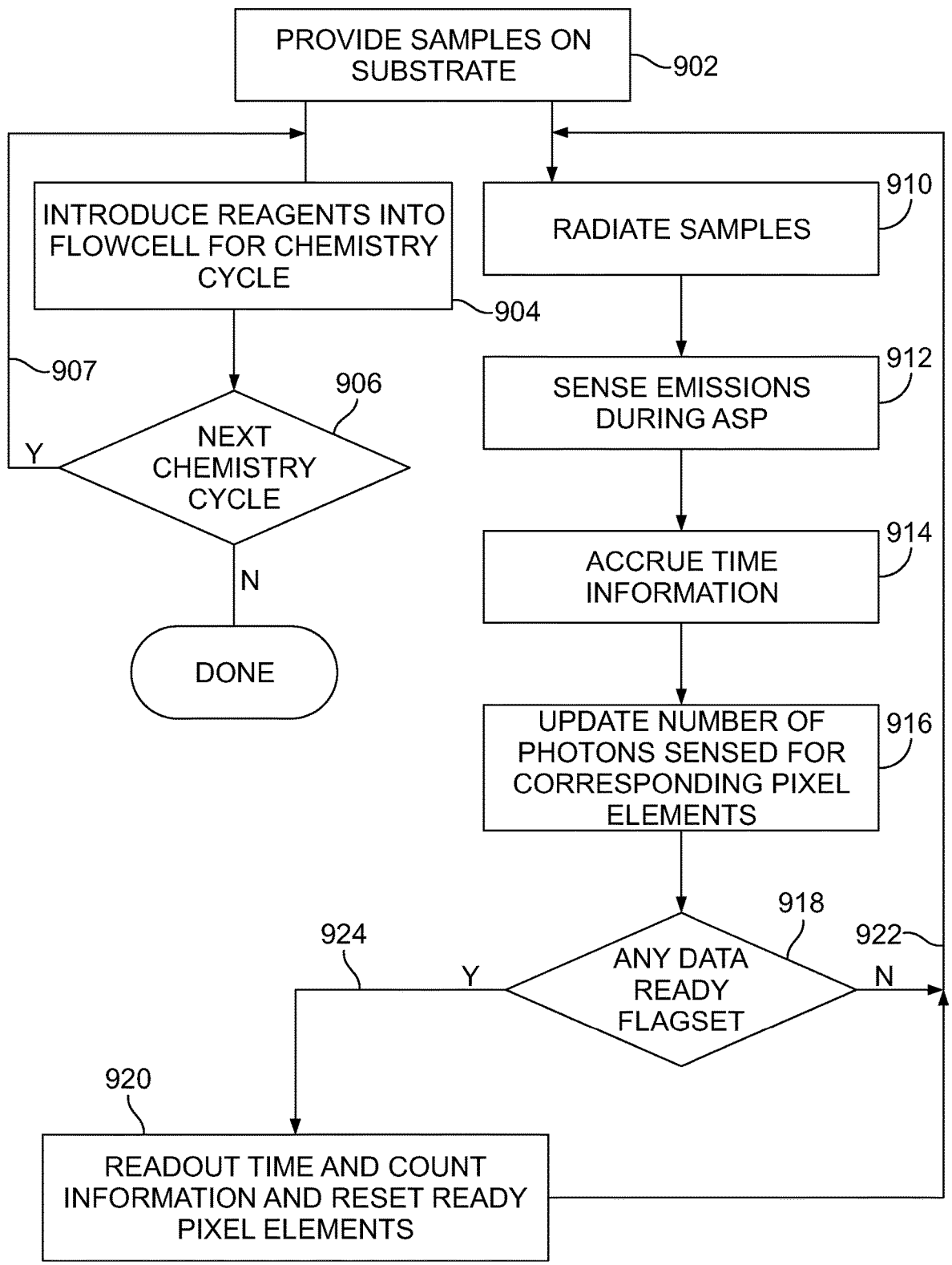
FIG. 8 illustrates a processing sequence carried out in accordance with an embodiment for providing a real-time detection session in a non-synchronized manner in parallel with the chemistry cycles of a sequencing process.

FIG. 8 illustrates a processing sequence carried out in accordance with an embodiment for providing a real-time detection session in a non-synchronized manner in parallel with the chemistry cycles of a sequencing process. At 902, a substrate is provided in the flow cell with samples on the substrate. FIG. 8 illustrates parallel processing paths, namely a chemistry path 904-906 and a detection path 910-920. The chemistry path 904-906 and detection path 910-920 are performed in parallel in a non-synchronous manner, namely the process moves between operations 904 and 906 based on the chemistry timing which is separate and distinct and independent of a timing associated with the detection operations at 910-920.

At 904 one or more reagents are introduced into the DFP device 130 in connection with a current chemistry cycle. Reagents can include, for example, one or more of those set forth above in regard to FIG. 6 or below in regard to various sequencing protocols (including reagents set forth in the related references). At 906, it is determined whether additional chemistry cycles are to be performed in connection with a current sequencing process. If so, flow moves along 907 and the next reagent or reagents are introduced through the DFP device 130 in connection with the next chemistry cycle. The operations at 904 and 906 are repeated until the sequencing process is done.

At 910, the detection session begins by radiating the samples from the excitation assembly 112. At 912, the IC photon detection layer 155 senses photons emitted from the labels during an active sensing period. At 914, the temporal accumulator 428 for each tixel 160 that receives a photon increases the accrued time information based on the photon TOA count. At 916, each tixel 160, that receives a photon, updates the number of photons detected by the tixel 160 during the current sample set inspection frame.

At 918, the read out controller 151 checks each tixel 160 to determine whether the data ready flag 445 has been set. Individual data ready flags 471 are set when the corresponding tixel 160 senses a number of photons that equals or exceeds a predetermined photon limit. The predetermined photon limit may be programmable or set at the time of manufacture. When data ready flags 431 are set, flow moves along 924 to 920. At 920, the read out controller 151 reads out the time and count information for the tixels 170 having data ready flags 431. At 920, the read out controller 151 also resets the time information and the photon counter for these tixels 160. Next flow moves along 922.

Returning to 918, when it is determined that no data ready flags have been set, flow moves from 918 along 922 back to 910. The operations of 910-920 are continuously repeated based on detection session timing until the detection session is complete. The detection session timing is independent of the chemistry cycle timing.

The processes of FIG. 8 may be performed in connection with a functionalization layer 144 having a number of samples 167 that matches in a one to one relation with the number of spot beams 120 and pixel elements 170. When a one to one relation exists between samples 167 and pixel elements 170, the functionalization layer 144 does not move between sample 134 sets. Optionally, the processes of FIG. 8 may be performed in connection with a functionalization layer 144 having a larger number of samples 167 than the number of spot beams 120 and pixel elements 170. When a one to one relation does not exist between samples 167 and pixel elements 170, the functionalization layer 144 is moved between sample sets by the stage 139.

Figure 9:
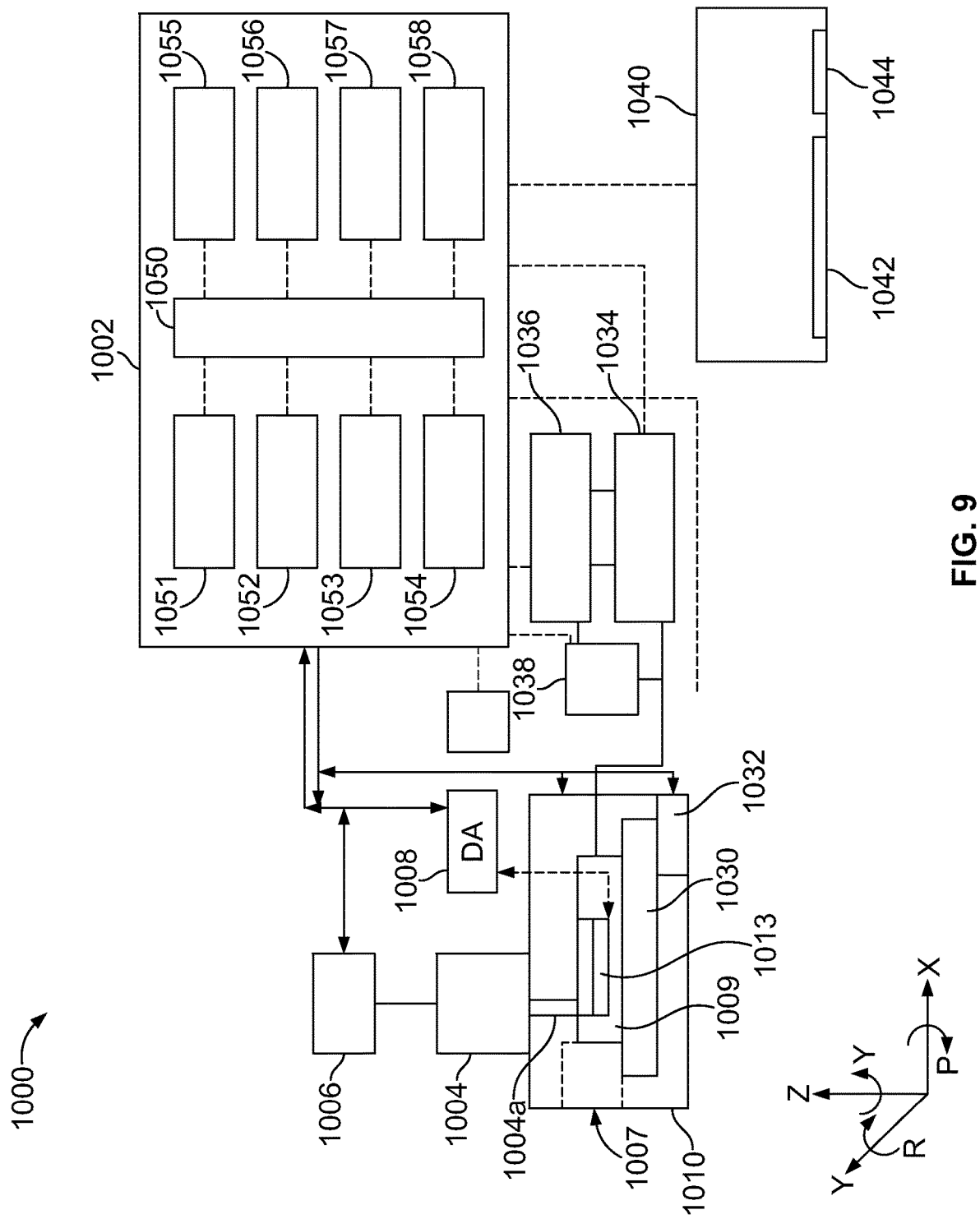
FIG. 9 is a block diagram of an assay system for biological or chemical analysis formed in accordance with one embodiment.

FIG. 9 is a block diagram of an assay system 1000 for biological or chemical analysis formed in accordance with one embodiment. In some embodiments, the assay system 1000 is a workstation that may be similar to a bench-top device or desktop computer. For example, a majority of the systems and components for conducting the desired reactions can be within a common housing of the assay system 1000. In some embodiments, the assay system 1000 includes one or more components, assemblies, or systems that are remotely located from the assay system 1000. Furthermore, the assay system 1000 may include various components, assemblies, and systems (or sub-systems) that interact with each other to perform one or more predetermined methods or assay protocols for biological or chemical analysis.

For example, the assay system 1000 includes a system controller 1002 that may communicate with the various components, assemblies, and sub-systems of the assay system 1000. As shown, the assay system 1000 has an optical assembly 1004, an excitation source assembly 1006, a detector assembly 1008, and a docking station or system 1010 that supports one or more cartridges 1009 loaded through a port 1007. The cartridge 1009 has one or more DFP devices 1013 secured therein. The DFP device 1013 includes the structures discussed above. In some embodiments, the optical assembly 1004 is configured to direct incident light from the excitation source assembly 1006, through a laser beam channel 1004a, onto one or more gratings along edges of the DFP device(s) 1013. The excitation source assembly 1006 may include one or more excitation light sources that are configured to excite labels associated with the samples in the DFP device 1013. As explained above, the samples emit photons that are detected by the DFP device 1013.

The cartridge 1009 and the laser guide 1004a may be moved relative to each other in order to align the laser guide 1004a and the gratings on the edges of the DFP devices 1013. The cartridge 1009 and the laser guide 1004a may be moved also to adjust an optical coupling angle between the laser guide 1004a and a surface of the gratings. In particular embodiments, the docking system 1010 includes a cartridge stage 1030 and a motor assembly 1032. The motor assembly 1032 moves the cartridge stage 1030 (and the cartridge 1009 thereon) with respect to the laser guide 1004a. In other embodiments, the laser guide 1004a may be moved in addition to or alternatively to, the cartridge stage 1030 (and the cartridge 1009 thereon).

Optionally, the cartridge stage 1030 may be adjusted linearly horizontally and/or vertically, such as translating along one or more of X, Y and Z planes. Optionally, the cartridge stage 1030 may be adjusted rotationally, such as rotated about one or more of X, Y and Z planes, as denoted by the pitch (P), roll (R), and yaw (Y) arrows. The cartridge stage 1030 is adjusted to provide a preferred coupling angle between the light source and gratings. The adjustments can be attained through an iteratively, active alignment process.

During active alignment, the DFP device 1013 is used to record the coupling efficiency and thus an external monitor is not required. Light is coupled through the grating and propagates in channel waveguides which are either in contact with the solution or isolated. The amount of scattered light is proportional to the amount of light propagating in the wave guide. Thus, the amount of scattered light is proportional to the coupling efficiency. During active alignment, the tixels on the DFP device 1013 are armed to be sensitive to light while all or a portion of a laser pulse is emitted. The amount of light, and/or the degree of overlap in time between laser excitation and the pixel detection window may be controlled such that the pixel elements of the DFP device 1013 do not saturate the event counters. The DFP device 1013 can count an amount of light incident thereon during this active alignment process.

The coupling angle is changed by changing the position and orientation of the cartridge stage 1030 at the direction of the system controller 1002. The system controller 1002 implements a search algorithm that searches for the angle that affords the desired (e.g., highest) amount of scattered light which is the position of desired (e.g., highest) coupling efficiency. This scheme may be used either once for a one-time alignment between the laser array and inserted cartridge 1009, or periodically or continuously during a run in order to compensate for wavelength drift by the laser or other mechanical or thermal drifts.

Also shown, the assay system 1000 may include a fluidic control system to control the flow of fluid throughout a fluidic network 1035 (indicated by the solid lines) of the assay system 1000. The fluidic control system 1034 may deliver reagents to the DFP device 1013 during, for example, a sequencing protocol. The assay system 1000 may also include a fluid storage system 1036 that is configured to hold fluids that may be used by the assay system 1000 and a temperature control system 1038 that regulates the temperature of the fluid. The temperature control system 1038 may also generally regulate a temperature of the assay system 1000 using, for example, heat sinks and blowers. Exemplary temperature control systems are described in U.S. Ser. No. 12/565,606, which is incorporated herein by reference.

Also shown, the assay system 1000 may include a user interface 1040 that interacts with the user. For example, the user interface 1040 may include a display 1042 to display or request information from a user and a user input device 1044 to receive user inputs. In some embodiments, the display 1042 and the user input device 1044 are the same device (e.g., touchscreen). As will be discussed in greater detail below, the assay system 1000 may communicate with various components to perform the desired reactions. The assay system 1000 may also be configured to analyze the detection data to provide a user with desired information.

The fluidic control system 1034 is configured to direct and regulate the flow of one or more fluids through the fluidic network 1035. The fluidic network 1035 may be in fluid communication with at least one of the samples or DFP devices 1013 and the fluid storage system 1036. For example, select fluids may be drawn from the fluid storage system 1036 and directed to the sample or DFP device 1013 in a controlled manner, or the fluids may be drawn from the sample or DFP device 1013 and directed toward, for example, a waste reservoir in the fluid storage system 1036. Although not shown, the fluidic control system 1034 may include flow sensors that detect a flow rate or pressure of the fluids within the fluid network. The sensors may communicate with the system controller 1002.

The temperature control system 1038 is configured to regulate the temperature of fluids at different regions of the fluidic network 1035, the fluid storage system 1036, and/or the DFP device 1013. For example, the temperature control system 1038 may include a thermocycler (not shown) that interfaces with the DFP device 1013 and controls the temperature of the fluid that flows along the DFP device 1013. The temperature control system 1038 may also regulate the temperature of solid elements or components of the assay system 1000, DFP device 1013 or sample. Although not shown, the temperature control system 1038 may include sensors to detect the temperature of the fluid or other components. The sensors may communicate with the system controller 1002.

The temperature control system 1038 is configured to regulate the temperature of fluids at different regions of the fluidic network 1035, the fluid storage system 1036, and/or the DFP device 1012. For example, the temperature control system 1038 may include a thermocycler (not shown) that interfaces with the DFP device 1012 and controls the temperature of the fluid that flows along the DFP device 1012. The temperature control system 1038 may also regulate the temperature of solid elements or components of the assay system 1000, DFP device 1012 or sample. Although not shown, the temperature control system 1038 may include sensors to detect the temperature of the fluid or other components. The sensors may communicate with the system controller 1002.

The fluid storage system 1036 is in fluid communication with the sample 1013 and may store various reaction components or reactants that are used to conduct the desired reactions therein. The fluid storage system 1036 may store fluids for washing or cleaning the fluidic network 1035 or the DFP device 1013 and also for diluting the reactants. For example, the fluid storage system 1036 may include various reservoirs to store reagents, enzymes, other biomolecules, buffer solutions, aqueous, and non-polar solutions, and the like. Furthermore, the fluid storage system 1036 may also include waste reservoirs for receiving waste products.

The docking system 1010 is configured to engage one or more DFP devices 1013, for example, in at least one of a mechanical, electrical, and fluidic manner. The docking system 1010 may hold the DFP device(s) 1013 in a desired orientation to facilitate the flow of fluid through the sample and/or detection of the sample. Docking systems can be configured to deliver fluids to one sample, but not to another. The system can be configured to deliver different fluids to different samples. Alternatively or additionally, fluids can be delivered to different samples in a different temporal sequence, amount, flow rate, or duration.

The system controller 1002 may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. The above examples are exemplary only, and are thus not necessarily intended to limit in any way the definition and/or meaning of the term system controller. In the exemplary embodiment, the system controller 1002 executes a set of instructions that are stored in one or more storage elements, memories, or modules in order to at least one of obtain and analyze detection data. Storage elements may be in the form of information sources or physical memory elements within the assay system 1000.

The set of instructions may include various commands that instruct the assay system 1000 to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the assay system 1000, processed in response to user inputs, or processed in response to a request made by another processing machine (e.g., a remote request through a communication link).

The system controller 1002 may be connected to the other components or sub-systems of the assay system 1000 via communication links (indicated by dashed lines). The system controller 1002 may also be communicatively connected to off-site systems or servers. The communication links may be hardwired or wireless. The system controller 1002 may receive user inputs or commands, from the user interface 1040. The user input device 1044 may include a keyboard, mouse, a touch-screen panel, and/or a voice recognition system, and the like. Alternatively or in addition, the user input device 1044 may also be the display.

In some embodiments, the assay system 1000 may have interchangeable or swappable devices (e.g., plug-and-play). For example, the docking system 1010 or cartridge stage 1030 may be readily replaced or substituted with a different docking system 1010 or cartridge stage 1030. This may occur when a different type of DFP device 1013 is desired to be used. In some embodiments, the DFP device 1013 is readily exchanged from the cartridge stage 1030. Furthermore, the fluid storage system 1036 may be a container that is readily separated from the fluid network and replaced by another container. This may occur when the fluid in the container is depleted, has expired, or a different container is required because a user of the assay system 1000 desires to run a different assay protocol. Furthermore, the system controller 1002 may have swappable devices (e.g., if the user desires to use the assay system 1000 to execute a different assay protocol).

FIG. 9 also illustrates a block diagram of the system controller 1002. In one embodiment, the system controller 1002 includes one or more processors or modules that can communicate with one another. The system controller 1002 is illustrated conceptually as a collection of modules, but may be implemented utilizing any combination of dedicated hardware boards, DSPs, processors, etc. Alternatively, the system controller 1002 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

The system controller 1002 may include a plurality of modules 1051-1058 that communicate with a system control module 1050. The system control module 1050 may communicate with the user interface 1040. Although the modules 1051-1058 are shown as communicating directly with the system control module 1050, the modules 1051-1058 may also communicate directly with each other, the user interface 1040, or the other systems. Also, the modules 1051-1058 may communicate with the system control module 1050 through the other modules.

The plurality of modules 1051-1058 include system modules 1051-1053 that communicate with the sub-systems. The fluidic control module 1051 may communicate with the fluidic control system 1034 to control the valves and flow sensors of the fluidic network 1035 for controlling the flow of one or more fluids through the fluidic network 1035. The fluid storage module 1052 may notify the user when fluids are low or when the waste reservoir must be replaced. The fluid storage module 1052 may also communicate with the temperature control module so that the fluids may be stored at a desired temperature.

The plurality of modules 1051-1058 may also include an optics adjustment (or correction) module 1054 that communicates with the optics adjustment system 1020 and an identification module 1055 that determines identification information relating to the sample or substrate that bears the sample 1013. For example, the DFP device 1013 may be detected or scanned before a detection session or before being placed onto the cartridge stage 1030 to identify the sample or substrate 1013. The optics adjustment module 1054 may communicate with the various devices that are capable of selectively moving the optical components, such as a transfer device or a rotatable optical device. The plurality of modules 1051-1058 may also include a detection data analysis module 1058 that receives and analyzes the detection data (e.g., image data) from the detector assembly 1008. The processed detection data may be stored for subsequent analysis or may be transmitted to the user interface 1040 to display desired information to the user. Furthermore, there may be a sample module that communicates with the sample (e.g., receives signals regarding temperature of the sample or flow rate of a fluid in the sample).

Protocol modules 1056 and 1057 communicate with the system control module 1050 to control the operation of the sub-systems when conducting predetermined assay protocols. The protocol modules 1056 and 1057 may include sets of instructions for instructing the assay system 1000 to perform specific operations pursuant to predetermined protocols. The protocol modules 1056 and 1057 include a sequencing-by-synthesis (SBS) module 1056 that may be configured to issue various commands for performing sequencing-by-synthesis processes. In some embodiments, the SBS module 1056 may also process detection data. The protocol module 1057 may be configured to scan microarrays or perform other assay protocols.

By way of one example, the SBS module 1056 may be configured to issue commands for sequencing-by-synthesis processes. The sequencing-by-synthesis process may or may not include a step of amplifying templates for subsequent sequencing. For example, the SBS module 1056 may issue commands to perform bridge PCR where clusters of clonal amplicons are formed on localized areas of a DFP device, for example, within a channel (or lane) of a flow cell. After generating the amplicons through bridge PCR, the SBS module 1056 may provide instructions to linearize or denature the amplicons to make sstDNA and to add a sequencing primer such that the sequencing primer may be hybridized to a universal sequence that flanks a region of interest. Each sequencing cycle extends the sstDNA by a single base and is accomplished by a DNA polymerase and a mixture of four types of nucleotides, delivery of which can be instructed by the SBS module 1056. The different types of nucleotides have unique fluorescent labels, and each nucleotide can optionally have a reversible terminator that allows only a single-base incorporation to occur in each cycle. After one or more nucleotides are added to the sstDNA, the SBS module 1056 may instruct a wash step to remove nonincorporated nucleotides by flowing a wash solution through the flow cell. The SBS module 1056 may further instruct the excitation source assembly and detector assembly to perform a detection step to distinguish fluorophores based on different fluorescent lifetimes. After detection, the SBS module 1056 may optionally instruct delivery of a deblocking reagent to chemically cleave the fluorescent label and the terminator from the sstDNA, for example, if a reversible terminator technique is being used. The SBS module 1056 may instruct a wash step to remove the deblocking reagent and products of the deblocking reaction. Another similar sequencing cycle may follow. In such a sequencing protocol, the SBS module 1056 may instruct the fluidic control system 1034 to direct a flow of reagent and enzyme solutions through or over the DFP device 1013.

In some embodiments, the SBS module 1056 may also be configured to issue various commands for performing the steps of a sequencing protocol. In this case, the DFP device 1013 may include millions of wells where each well has a single capture bead having clonally amplified sstDNA thereon. Each well may also include other smaller beads that, for example, may carry immobilized enzymes (e.g., ATP sulfurylase and luciferase useful in a pyrosequencing protocol) or facilitate holding the capture bead in the well. The SBS module 1056 may be configured to issue commands to the fluidic control module to run consecutive cycles of fluids that carry a single type of nucleotide (e.g., 1st cycle: A; 2nd cycle: G; 3rd cycle: C; 4th cycle: T; 5th cycle: A; 6th cycle: G; 7th cycle: C; 8th cycle: T; and on). When a nucleotide is incorporated into the DNA during a pyrosequencing protocol, pyrophosphate is released thereby instigating a chain reaction where a burst of light is generated. The burst of light may be detected by a sample detector of the detector assembly. Detection data may be communicated to the system control module 1050, the detection data analysis module 1058, and/or the SBS module 1056 for processing. In some embodiments, incorporation of a nucleotide into DNA recruits an optical label that is detected or otherwise results in generation of an optical signal from an optical label. The detection data may be stored for later analysis or may be analyzed by the system controller 1002 and detection data may be sent to the user interface 1040.

The protocol module 1057 may be configured to send instructions for scanning a microarray for an unknown analyte. Before or after performing a detection session, the protocol module 1057 may instruct the optics adjustment system 1200 to move an optical component within, into, or out of the optical path. For example, the protocol module 1057 may request that the path compensator 1022 be inserted into or removed from the optical path. The protocol module 1057 may also request that another optical component be repositioned. Any of a variety of movable or adjustable optical components set forth herein can be moved, adjusted or otherwise manipulated in response to instructions sent from protocol module 1057 or any other appropriate module of a system controller. Once the collective arrangement of the optical components is established as desired, the protocol module 1057 may instruct the excitation source assembly to provide incident light onto the samples and the detector assembly to detect the optical signals provided by the sample.

In some embodiments, the user may provide user inputs through the user interface 1040 to select an assay protocol to be run by the assay system 1000. In other embodiments, the assay system 1000 may automatically detect the type of sample or DFP device 1013 that has been inserted into the docking system 1010 and confirm with the user the assay protocol to be run. Alternatively, the assay system 1000 may offer a limited number of assay protocols that could be run with the determined type of sample or DFP device 1013. The user may select the desired assay protocol, and the assay system 1000 may then perform the selected assay protocol based on preprogrammed instructions.

However, the assay system 1000 may also allow the user to reconfigure an assay protocol. After determining the assay protocol to run, the assay system 1000 may offer options to the user through the user interface 1040 for modifying the determined protocol. For example, if it is determined that the DFP device 1013 is to be used for amplification, the assay system 1000 may request a temperature or cycle of temperature changes for the amplification process. Furthermore, the assay system 1000 may issue warnings to a user if a user has provided user inputs that are generally not acceptable for the selected assay protocol. Furthermore, in other embodiments, the assay system 1000 may establish or request user inputs to establish a priority status of each sample or DFP device 1013 in the assay system 1000. The assay system 1000 may then operate according to the priority statuses of the samples or DFP devices 1013 therein. For example, the sequencing protocols may have a higher priority than an amplification protocol. According to selected priorities the assay system can run on a schedule that pauses lower priority samples when a schedule conflict arises.

The SPAD system may be used as a multi-chemistry assay whereby, when a chemistry without lifetime information is used, only photon counts are used to determine the existence of a base (e.g., by using multiple lasers or by sequentially flowing labeled nucleotides such as in a pyrosequencing chemistry).

Any of a variety of microarrays known in the art or techniques for their manufacture, including, for example, those set forth herein, can be used. A typical microarray contains addressable locations, sometimes referred to as sites or features, each having a population of probes. The population of probes at each site is typically homogenous having a single species of probe, but in some embodiments the populations can each be heterogeneous. Sites or features of an array are typically discrete, being separated with spaces between each other but can also be contiguous. The size of the probe sites and/or spacing between the sites can vary such that arrays can be high density, medium density or lower density. High density arrays are characterized as having sites separated by less than about 15 µm. Medium density arrays have sites separated by about 15 to 30 µm, while low density arrays have sites separated by greater than 30 µm. An array useful in the invention can have sites that are separated by less than 100 µm, 50 µm, 10 µm, 5 µm, 1 µm, or 0.5 µm. An apparatus or method of an embodiment of the invention can be used to image an array at a resolution sufficient to distinguish sites at the above densities or density ranges.

Further examples of commercially available microarrays and techniques for their manufacture include, for example, an Affymetrix® GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482, 867; 5,491,074; 5,624,711; 5,795,716; 5,831,070; 5,856, 101; 5,858,659; 5,874,219; 5,968,740; 5,974,164; 5,981, 185; 5,981,956; 6,025,601; 6,033,860; 6,090,555; 6,136, 269; 6,022,963; 6,083,697; 6,291,183; 6,309,831; 6,416, 949; 6,428,752 and 6,482,591, each of which is hereby incorporated by reference. A spotted microarray can also be used in a method according to an embodiment of the invention as can the spotting techniques that are used to make such arrays. An exemplary spotted microarray is a CodeLink™ Array available from Amersham Biosciences.

Another microarray that is useful is one that is manufactured using inkjet printing methods such as SurePrint™ Technology available from Agilent Technologies.

The systems and methods set forth herein can be used to detect the presence of a particular target molecule in a sample contacted with a nucleic acid probe. This can be determined, for example, based on binding of a labeled target analyte to a particular probe of the microarray or due to a target-dependent modification of a particular probe to incorporate, remove, or alter a label at the probe location. A protocol for biological or chemical analysis that is used herein can include any one of several assays can be used to identify or characterize targets using a microarray as described, for example, in U.S. Patent Application Publication Nos. 2003/0108867; 2003/0108900; 2003/0170684; 2003/0207295; or 2005/0181394, each of which is hereby incorporated by reference.

Furthermore, apparatus and systems described herein may be constructed to include various components and assemblies as described in PCT application PCT/US07/07991, entitled "System and Devices for Sequence by Synthesis Analysis", filed Mar. 30, 2007 and/or to include various components and assemblies as described in International Publication No. WO 2009/042862, entitled "Fluorescence Excitation and Detection System and Method", filed Sep. 26, 2008, both of which the complete subject matter are incorporated herein by reference in their entirety. In particular embodiments, optical systems can include various components and assemblies as described in U.S. Pat. No. 7,329,860 and WO 2009/137435, of which the complete subject matter is incorporated herein by reference in their entirety. Optical systems can also include various components and assemblies as described in U.S. patent application Ser. No. 12/638,770, filed on Dec. 15, 2009, of which the complete subject matter is incorporated herein by reference in its entirety. Particularly useful components from the aforementioned references are those included in the fluidics systems for delivering sequence reagents to a substrate, optical systems related to excitation of fluorescently labeled samples on a substrate and control systems for carrying out desired protocols for biological and chemical analysis. Other components are useful as well.

In particular embodiments, methods, and optical systems described herein may be used for sequencing nucleic acids. For example, sequencing-by-synthesis (SBS) protocols are particularly applicable. In SBS, a plurality of fluorescently labeled modified nucleotides can be used to sequence single nucleic acid molecules that are spatially separated from each other on a substrate for single molecule detection. SBS can also be used to sequence ensembles of nucleic acids, wherein several copies of a particular sequence form dense clusters of amplified DNA. Several clusters (possibly millions of clusters) can be present on the surface of a substrate (e.g., a surface that at least partially defines a channel in a flow cell). Thus, samples for sequencing in a method or apparatus set forth herein can take the form of single nucleic acid molecules that are separated from each other so as to be individually resolvable, amplified populations of nucleic acid molecules in the form of clusters or other features, or beads that are attached to one or more molecules of nucleic acid.

For SBS protocols, nucleic acids can be prepared such that they comprise an oligonucleotide primer adjacent to an unknown target sequence. To initiate the first SBS sequencing cycle, one or more differently labeled nucleotides, and DNA polymerase, etc., can be flowed into/through the flow cell by a fluid flow subsystem (not shown). Either a single type of nucleotide can be added at a time, or the nucleotides used in the sequencing procedure can be specially designed to possess a reversible termination property, thus allowing each cycle of the sequencing reaction to occur simultaneously in the presence of several types of labeled nucleotides (e.g. A, C, T, G). The nucleotides can include detectable label moieties such as fluorophores. Where the four nucleotides are mixed together, the polymerase is able to select the correct base to incorporate and each sequence is extended by a single base. Nonincorporated nucleotides can be washed away by flowing a wash solution through the flow cell. One or more lasers may excite the nucleic acids and induce fluorescence. The fluorescence emitted from the nucleic acids is based upon the fluorophores of the incorporated base, and different fluorophores may produce emissions having different fluorescence lifetimes that can be distinguished using apparatus and methods set forth herein. A deblocking reagent can be introduced to remove reversible terminator groups and/or fluorescent labels from the DNA strands that were extended and detected. The deblocking reagent can then be removed using a wash solution. The nucleic acid sample is then ready for a further cycle of sequencing starting with introduction of a labeled nucleotide as set forth above. The fluidic and detection steps can be repeated several times to complete a sequencing run. Exemplary sequencing chemistries and reagents are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

In some embodiments, nucleic acids can be attached to a surface and amplified prior to or during sequencing. For example, amplification can be carried out using bridge amplification. Useful bridge amplification methods are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420. Another useful method for amplifying nucleic acids on a surface is rolling circle amplification (RCA), for example, as described in Lizardi et al., Nat. Genet. 19:225-232 (1998) and US 2007/0099208 A1, each of which is incorporated herein by reference. Emulsion PCR on beads can also be used, for example as described in Dressman et al., Proc. Natl. Acad. Sci. USA 100:8817-8822 (2003), which is incorporated herein by reference.

Other sequencing techniques that are applicable for use of the methods and systems set forth herein are pyrosequencing, nanopore sequencing, and sequencing by ligation. Exemplary pyrosequencing techniques and samples that are particularly useful are described in U.S. Pat. Nos. 6,210,891; 6,258,568; 6,274,320 and Ronaghi, Genome Research 11:3-11 (2001), each of which is incorporated herein by reference. Exemplary nanopore techniques and samples that are also useful are described in Deamer et al., Acc. Chem. Res. 35:817-825 (2002); Li et al., Nat. Mater. 2:611-615 (2003); Soni et al., Clin Chem. 53:1996-2001 (2007) Healy et al., Nanomed. 2:459-481 (2007) and Cockroft et al., J. am. Chem. Soc. 130:818-820; and U.S. Pat. No. 7,001,792, each of which is incorporated herein by reference. In particular, these methods can utilize repeated steps of reagent delivery and detection, wherein emission from fluorescent labels can be detected and different labels distinguished based on fluorescence lifetime using apparatus and methods set forth herein. An instrument or method set forth herein can be configured with reservoirs, valves, fluidic lines and other fluidic components along with control systems for those components in order to introduce reagents and detect signals according to a desired protocol such as those set forth in the references cited above.

Exemplary labels that can be detected in accordance with various embodiments, for example, when present on or within a support structure include, but are not limited to, a; luminophore; fluorophore; fluorescent nanocrystal; or other moiety that can be detected based on an optical characteristic having a temporal decay. Fluorophores that may be useful include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue™, Texas Red, alexa dyes, phycoerythin, bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), or WO 98/59066, each of which is hereby incorporated by reference. In some embodiments, the one pair of labels may be excitable by a first excitation wavelength and another pair of labels may be excitable by a second excitation wavelength.

Labels can be attached to nucleotides or oligonucleotides, for example, as set forth above in regard to various SBS protocols and in the related references. Alternatively or additionally, one or more labels can be attached to a polymerase or ligase. For example, a first label can be attached to a polymerase and a second label can be attached to a nucleotide such that interaction between the labels can be detected using apparatus or methods set forth herein. The interaction between the first and second labels can be, for example, fluorescence resonance energy transfer (FRET) or quenching, and can be distinguished based on different interactions that occur for different labels on different nucleotide types. Exemplary reagents and labeling techniques that can be used are described in U.S. Pat. Nos. 7,329,492; 7,211,414; US 2007/0250274; US 2008/0091005 and WO 2009/056831, each of which is incorporated herein by reference in its entirety. In further embodiments, nucleotides need not include a label. Instead one or more labels that are attached to a polymerase can be detected and different nucleotide types distinguished based on their different effects on the polymerase label(s). Specifically, changes in the fluorescent lifetimes of labels that are attached to the polymerase that occur upon interactions of the polymerase with nucleotides can be detected using apparatus and methods set forth herein. Exemplary polymerase labeling schemes that can be used are described in WO 2010/068884, which is incorporated herein by reference in its entirety.

Although embodiments are exemplified with regard to detection of samples that include biological or chemical substances supported by an optical substrate, it will be understood that other samples can be detected by the embodiments described herein. Other exemplary samples include, but are not limited to, biological specimens such as cells or tissues, electronic chips such as those used in computer processors, and the like. Examples of some of the applications include microscopy, high-resolution reprographics, fluorescent image acquisition, analyzing and sequencing of nucleic acids, DNA sequencing, sequencing-by-synthesis, detection of microarrays, and the like.

In an embodiment, a photon detection integrated circuit, comprises a substrate having an array of time domain picture elements (tixels) formed therein. Each tixel comprises a photon time of arrival (TOA) detector element to sense photon arrival events over a plurality of active sensing periods. Each photon arrival event is sensed when a photon is incident on the detector element. Further, a temporal accumulator is provided to accumulate time interval information in connection with multiple photon arrival events that occur over the plurality of active sensing periods. An array of tixel output nodes is connected to corresponding tixels in the array of tixels. Each tixel output node conveys, from the corresponding tixel, a data value representing the accumulated time interval information accrued over the plurality of active sensing periods.

The photon TOA detect element constitutes one of an avalanche diode, a single photon avalanche diode and a silicon photo multiplier. Each of the tixels includes a data ready circuit that sets a data ready flag when a predetermine number of photon arrival events are sensed. The tixel output node for the corresponding tixel, outputs the data value when the data ready flag is set. The temporal accumulator accumulates at least one of a temporal center of mass, time-gate count ratios and time-gated photon flux associated with multiple photons sensed over the plurality of active sensing periods. The substrate constitutes a complementary metal oxide semiconductor (CMOS) substrate having an array of the TOA detector elements and temporal accumulators formed therein.

Embodiments of the present invention do not specifically rely on SBS chemistry. Any flow, (e.g., a Pacific Biosciences flow) where the reactions are on an immobilized substrate and where a fluorescence image needs to be, captures can be used with the sensors described herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "each" is used merely to specify one or more individual members of a group and does not necessarily refer to every member of a group unless explicitly stated otherwise. Further, the limitations of the following claims are not written in means—plus-function format and are not intended to be interpreted based on 35 U.S.C. § 112, sixth paragraph, unless and until such claim limitations expressly use the phrase "means for" followed by a statement of function void of further structure.

What is claimed is:

1. An integrated detection, flow cell and photonics (DFP) device, comprising:

a substrate having an array of pixel elements that sense photons during active sensing periods of a frame, the substrate and the pixel elements forming an integrated circuit (IC) photon detection layer, wherein each pixel element includes a single photon avalanche diode (SPAD) and an in-pixel detection circuit, wherein the in-pixel detection circuit includes:
a photon detector switch connected to an output node of the SPAD;
a temporal accumulator capacitor electrically connected to the photon detector switch, the temporal accumulator capacitor to output an analog voltage proportional to a sum of arrival times for the photons sensed by the SPAD during the frame;
an event counter switch connected to the output node of the SPAD; and
an event counter capacitor electrically connected to the event counter switch, the event counter capacitor to output an other analog voltage proportional to a number of photons sensed by the SPAD during the frame;
at least one wave guide formed on the IC photon detection layer as a photonics layer;
an optical isolation layer formed over at least a portion of the wave guide; and
a collection of photo resist (PR) walls patterned to define at least one flow cell channel that is configured to direct fluid along a fluid flow path, the at least one wave guide aligned to extend along the fluid flow path, the flow cell channel configured to receive samples at sample sites that align with the array of pixel elements.

2. The device of claim 1, further comprising a grating optically coupled to an end of the waveguide, the isolation layer formed on the grating between the grating and one of the PR walls of the collection of PR walls.

3. The device of claim 1, wherein the isolation layer is formed of silicon dioxide to decouple the waveguide from an outer PR wall that is formed above the waveguide, the outer PR wall being one of the collection of PR walls.

4. The device of claim 1, wherein the substrate constitutes a complementary metal oxide semiconductor (CMOS) substrate.

5. The device of claim 1, further comprising a functionalization layer disposed over the photonics layer, the functionalization layer having a designated pattern of sample sites that align with corresponding pixel elements of the array.

6. The device of claim 1, wherein the IC photon detection layer includes a mask layer having an inter metal dielectric (IMD) substrate with at least one blocking layer embedded within the IMD substrate, the blocking layer having an array of mask apertures there through and aligned with the pixel elements.

7. The device of claim 6, wherein the at least one blocking layer includes multiple opaque blocking layers stacked above one another and spaced vertically apart by gaps, the blocking layers having openings aligned with one another to form the mask apertures.

8. The device of claim 1, wherein the in-pixel detection circuit further includes a period activation switch connected to the photon detector switch, the period activation switch to define the active sensing periods by closing.

9. The device of claim 5, further comprising a mask layer positioned between the photonics layer and the pixel elements, the mask layer comprising a plurality of blocking sub-layers stacked with respect to one another, the blocking sub-layers having openings that align with one another to form mask apertures, wherein the mask apertures are aligned with the respective sample sites.

10. The device of claim 9, wherein the mask apertures are widened as the mask apertures extend from the sample sites to the corresponding pixel elements of the array.

11. The device of claim 10, wherein the openings of the blocking sub-layers are positioned such that each of the mask apertures has a parabolic cross-section.

12. The device of claim 1, further comprising a storage capacitor provided in or above the substrate and a switch to electrically connect the storage capacitor to at least one of the pixel elements to change the pixel element to an armed state in which the pixel element is sensitive to incident photons.

13. The device of claim 1 wherein the SPAR has a cathode connected to a positive direct current (DC) voltage supply and an anode connected to the output node that is electrically common with both a gate input of the photon detector switch and an other gate input of the event counter switch.

14. The device of claim 1 wherein:
the in-pixel detection circuit further includes a period activation switch electrically in series with the photon detector switch; and
the period activation switch closes to define the active sensing periods by being conductive to an electrical current.

15. The device of claim 14 wherein the photon detector switch is to receive, via the output node of the SPAD, a photon incident signal produced by the SPAD, the photon detector switch to close in response to the photon incident signal received from the SPAD, the photon detector switch, when closed, to conduct the electrical current from the period activation switch to the temporal accumulator capacitor.

16. The device of claim 14 wherein:
the electrical current conducted from the period activation switch and the photon detector switch is to be accumulated in the temporal accumulator capacitor as a time-related charge during detection of the photons;
readout circuitry is connected to the temporal accumulator capacitor;
the time-related charge accumulated in the temporal accumulator capacitor is readable as the analog voltage proportional to the sum of arrival times for the photons sensed by the SPAD during the frame; and
the analog voltage is an output to the readout circuitry connected to the temporal accumulator capacitor.

17. The device of claim 1 wherein:
the in-pixel detection circuit further includes an event count switch electrically in series with the event counter switch; and
the event count switch closes for a fixed interval during each of the active sensing periods to be conductive to an electric current.

18. The device of claim 17 wherein the event counter switch is to receive, via the output node of the SPAD, a photon incident signal produced by the SPAD, the event counter switch to close in response to the photon incident signal received from the SPAD, the event counter switch, when closed, to conduct the electric current from the event counter switch to the event counter capacitor.

19. The device of claim 17 wherein:
the electric current conducted from the event count switch and the event counter switch is to be accumulated in the event counter capacitor as a photon count-related charge during the active sensing periods of the frame;

readout circuitry is connected to the event counter capacitor;

the photon count-related charge accumulated in the event counter capacitor is readable as the other analog voltage proportional to the number of photons sensed by the SPAD during the frame; and the other analog voltage is an output to the readout circuitry connected to the event counter capacitor.

20. The device of claim 1 wherein the in-pixel detection circuit includes switches connected to the temporal accumulator capacitor and the event counter capacitor, the switches to close in response to a signal delivered by the readout circuitry, the switches, when closed, to output the analog voltage stored in the temporal accumulator capacitor and the other analog voltage stored in the event counter capacitor to the readout circuitry.

* * * * *

UNITED STATES PATENT AND TRADEMARK OFFICE
CERTIFICATE OF CORRECTION

PATENT NO. : 10,895,534 B2
APPLICATION NO. : 14/619287
DATED : January 19, 2021
INVENTOR(S) : Hod Finkelstein et al.

Page 1 of 1

It is certified that error appears in the above-identified patent and that said Letters Patent is hereby corrected as shown below:

In the Claims

In Column 42, Line 16, in Claim 13, delete "SPAR" and insert -- SPAD --, therefor.

Signed and Sealed this
Thirteenth Day of April, 2021

Drew Hirshfeld
*Performing the Functions and Duties of the
Under Secretary of Commerce for Intellectual Property and
Director of the United States Patent and Trademark Office*